United States Patent [19]

Namba et al.

[11] Patent Number: 4,762,413
[45] Date of Patent: Aug. 9, 1988

[54] METHOD AND APPARATUS FOR MEASURING IMMUNOLOGICAL REACTION WITH THE AID OF FLUCTUATION IN INTENSITY OF SCATTERED LIGHT

[75] Inventors: Akihiro Namba, Tokyo; Fumio Uchino, Hachioji; Hitoshi Tateoka, Hachioji; Masahiro Ohno, Hachioji; Outaro Ando, Hino; Kouichi Karaki, Fuchu; Tatsuo Nagasaki, Musashino, all of Japan

[73] Assignee: Olympus Optical Co., Ltd., Tokyo, Japan

[21] Appl. No.: 769,965

[22] Filed: Aug. 27, 1985

[30] Foreign Application Priority Data

| Sep. 7, 1984 | [JP] | Japan | 59-186282 |
| Sep. 7, 1984 | [JP] | Japan | 59-186283 |
| Sep. 7, 1984 | [JP] | Japan | 59-186284 |
| Sep. 7, 1984 | [JP] | Japan | 59-186285 |
| Sep. 7, 1984 | [JP] | Japan | 59-186286 |
| Sep. 8, 1984 | [JP] | Japan | 59-186253 |
| Sep. 8, 1984 | [JP] | Japan | 59-187254 |
| Sep. 8, 1984 | [JP] | Japan | 59-187255 |
| Sep. 8, 1984 | [JP] | Japan | 59-187256 |

[51] Int. Cl.⁴ .................. G01N 21/51; G01N 33/557; G01N 35/02
[52] U.S. Cl. ............................ 356/339; 250/574; 356/246; 356/341; 422/64; 422/73; 436/164
[58] Field of Search ............... 356/336, 338, 339, 341, 356/434, 427, 246; 250/564, 565, 574; 422/64, 65, 73; 436/164

[56] References Cited

U.S. PATENT DOCUMENTS

3,842,252  10/1974  Jakeman et al.
4,158,234   6/1979  Grandchamp.
4,305,925  12/1981  Kapmeyer et al. ............ 356/339 X

FOREIGN PATENT DOCUMENTS

2440376  3/1976  Fed. Rep. of Germany.

OTHER PUBLICATIONS

Davi, "Application of a Laser Self-beat Spectroscopic Technique . . . ", *J. Chem. Soc. Faraday Trans. II* (GB), vol.-70, pp. 700-708, 1974.
Alon et al., "Improving Light Beating Experiments by Dust Discrimination", *Rev. Sci. Instrum.* vol. 46, No. 4 pp. 388-390, Apr. 1975.
Cohen et al., "Immunoassay by Light Scattering Spectroscopy", *Immunochemistry*, vol. 12, pp. 349-351, 1975.
Article entitled "Specific Protein Analysis by Light-Scatter Measurement with a Miniature Centrifugal Fast Analyzer", by T. O. Tiffany, J. M. Parella, W. F. Johnson and C. A. Burtis.

*Primary Examiner*—Davis L. Willis
*Assistant Examiner*—Matthew W. Koren
*Attorney, Agent, or Firm*—Parkhurst & Oliff

[57] ABSTRACT

A coherent laser light flux is projected into a cell made of transparent quartz and light scattered from particles suspended in an antigen-antibody reaction liquid contained in the cell is detected by a photomultiplier by means of a collimator. An output electrical signal from the photomultiplier is sampled at different time instances and samplings are supplied to a fast Fourier transformer to derive a plurality of power spectrum densities of fluctuation in intensity of the scattered light. A plurality of power spectrum densities are averaged to generate a mean power spectrum density. An amount of antigen contained in the reaction liquid is measured in accordance with the mean power spectrum density.

25 Claims, 29 Drawing Sheets

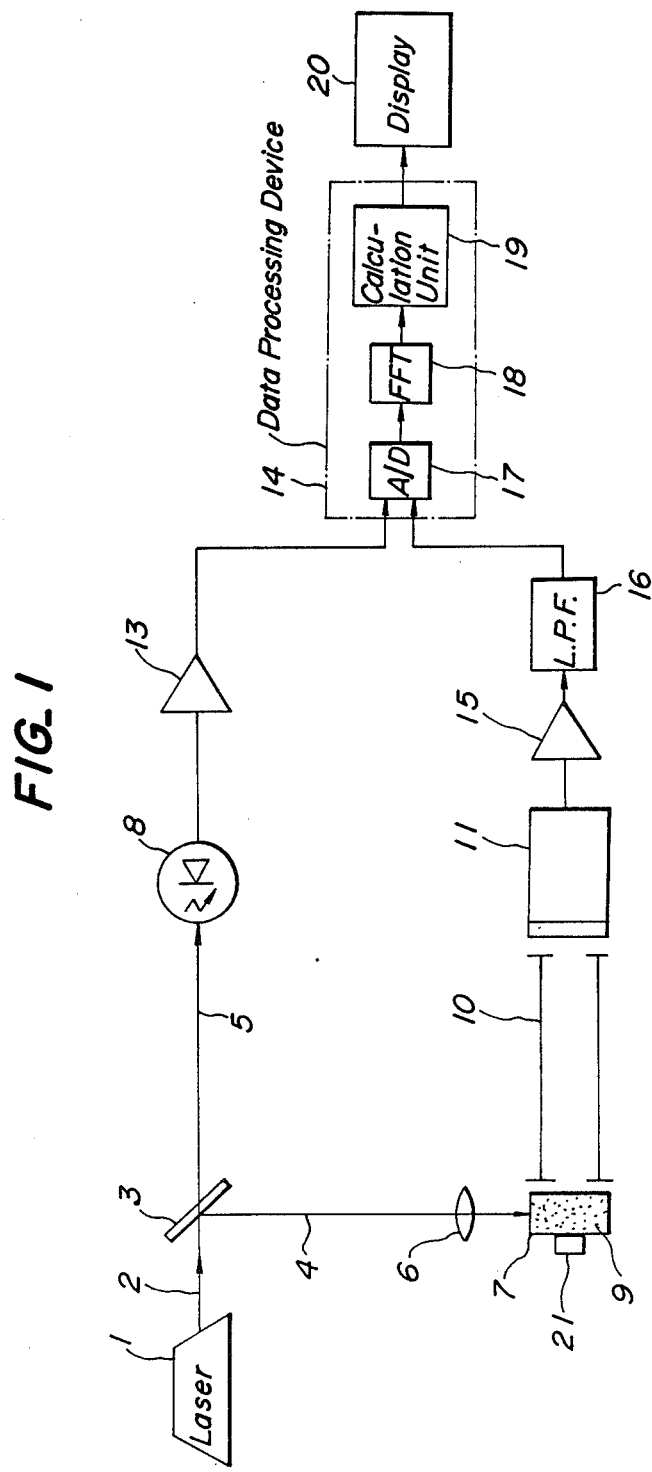

FIG_2
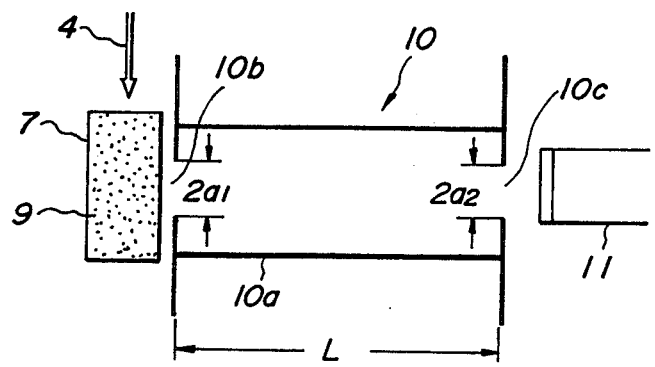
FIG_3
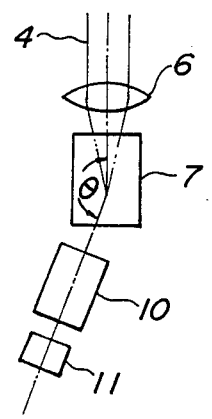

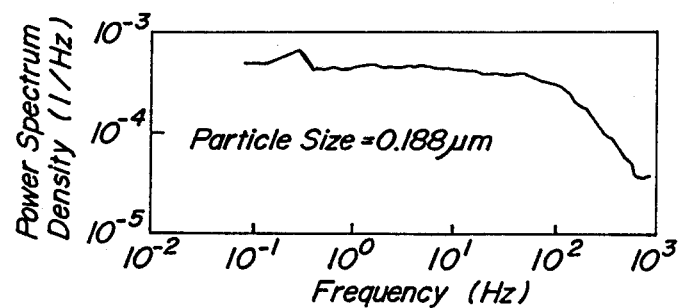
FIG_4
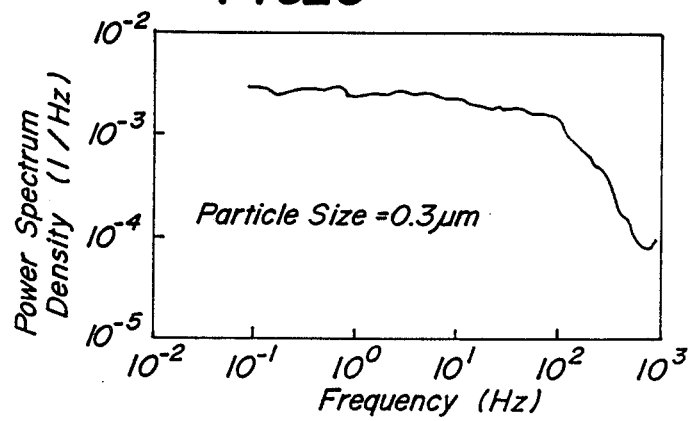
FIG_5
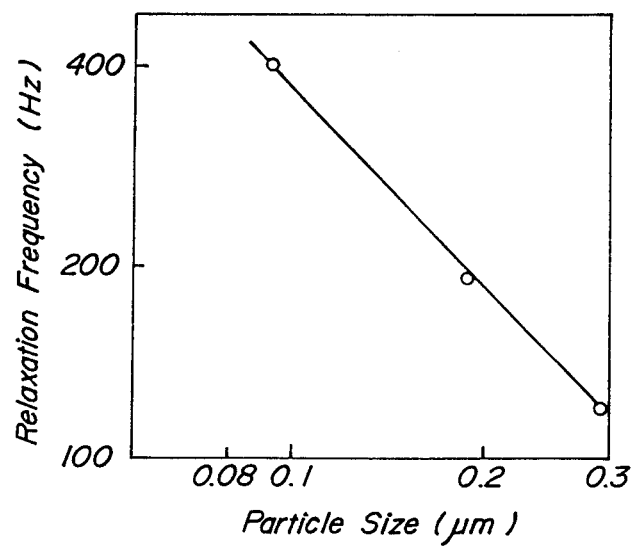
FIG_6

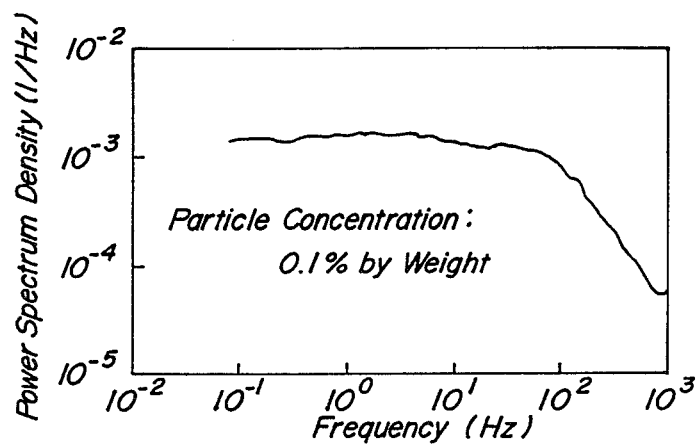
FIG_7
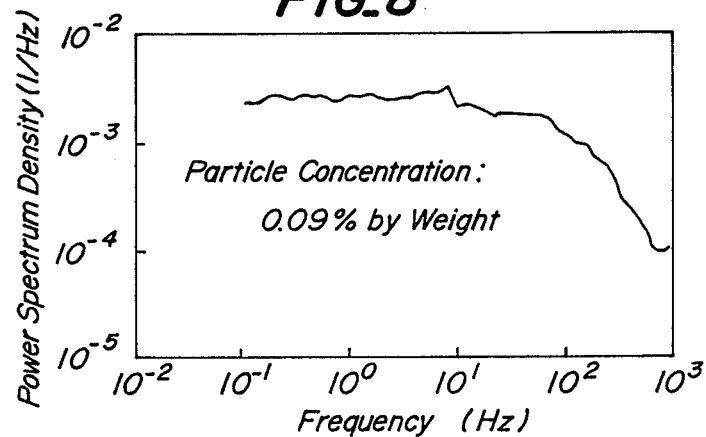
FIG_8
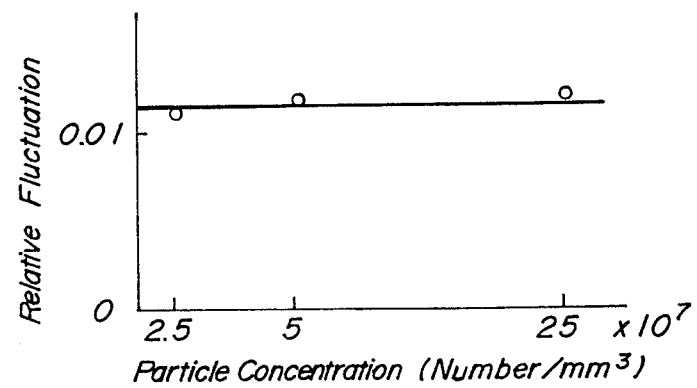
FIG_9

FIG_10
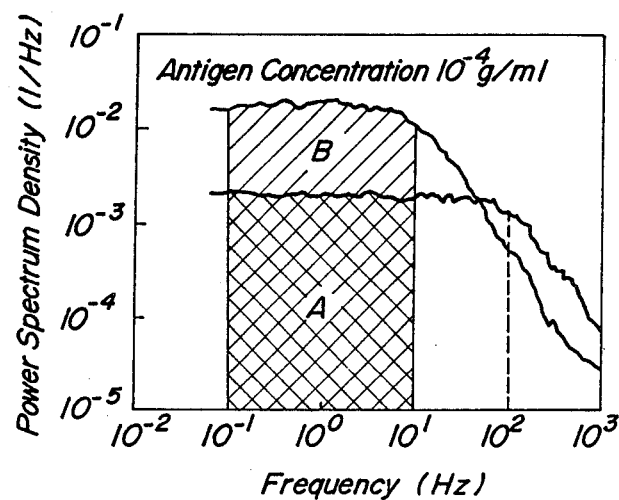
FIG_11
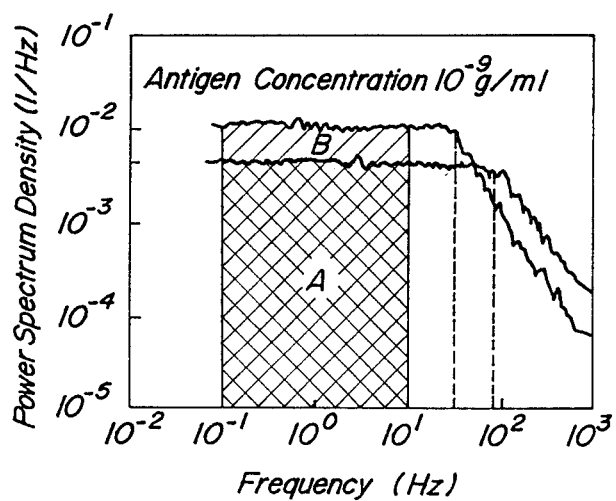

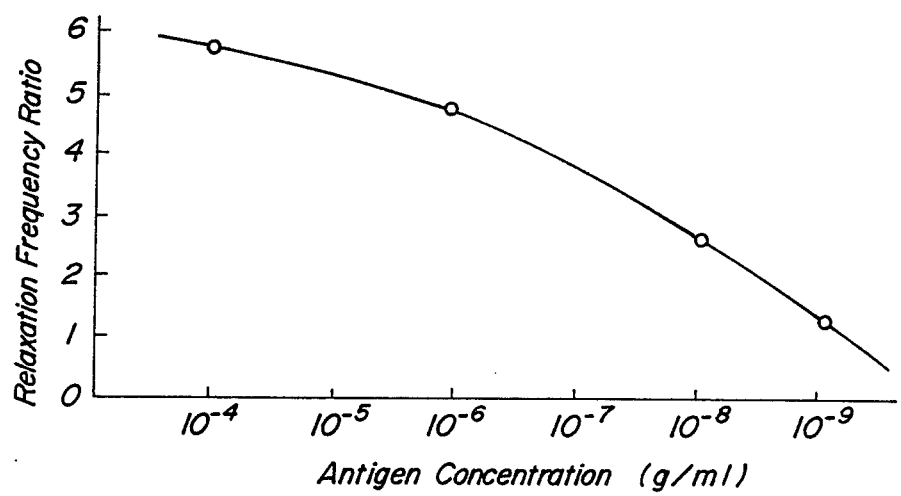
FIG_12
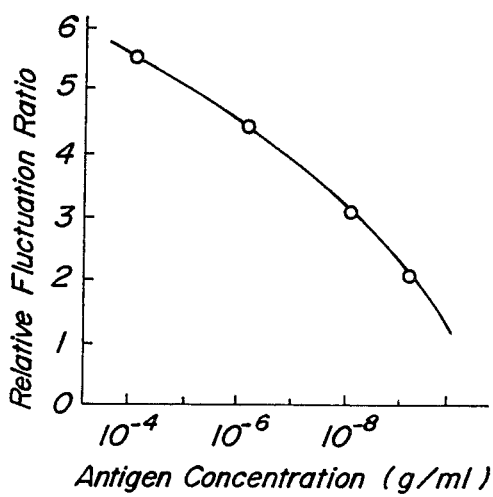
FIG_13

FIG_14
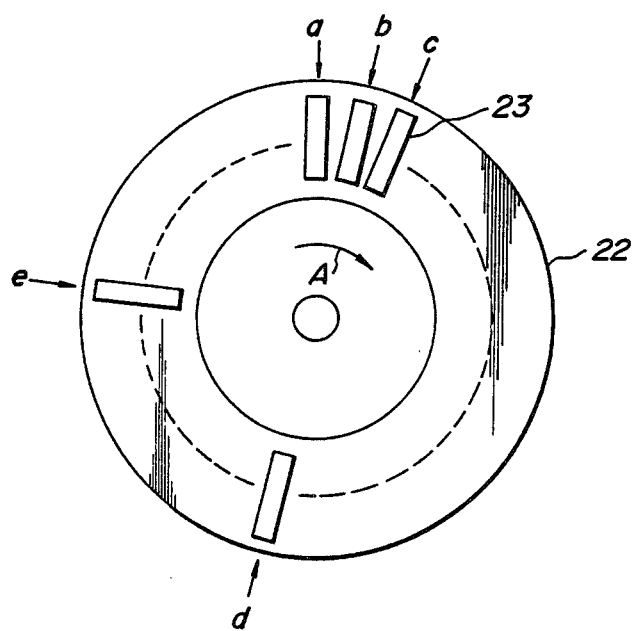
FIG_15
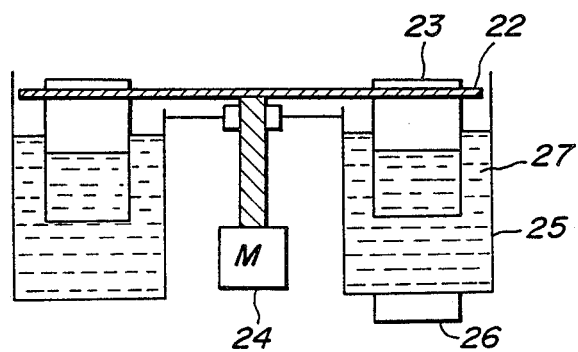

FIG_16
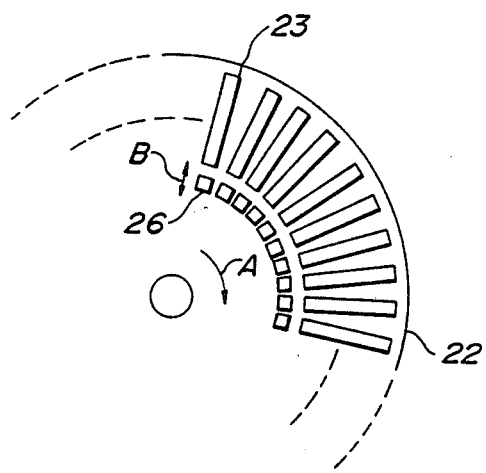
FIG_17
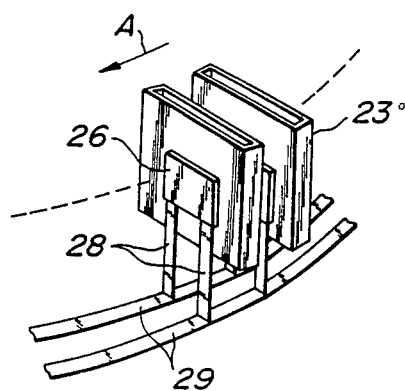

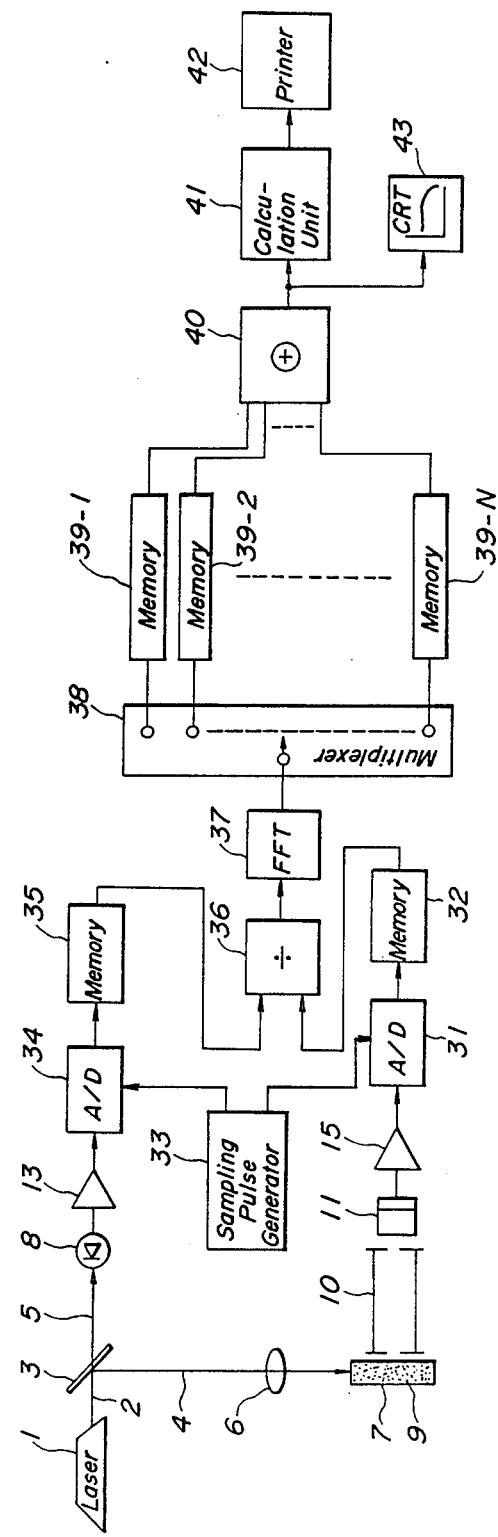

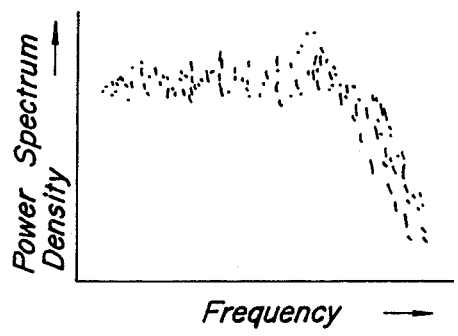 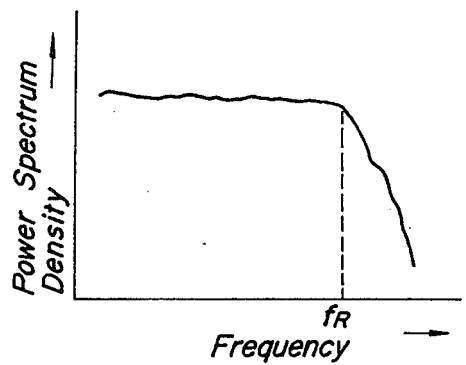
FIG_19A  FIG_19B

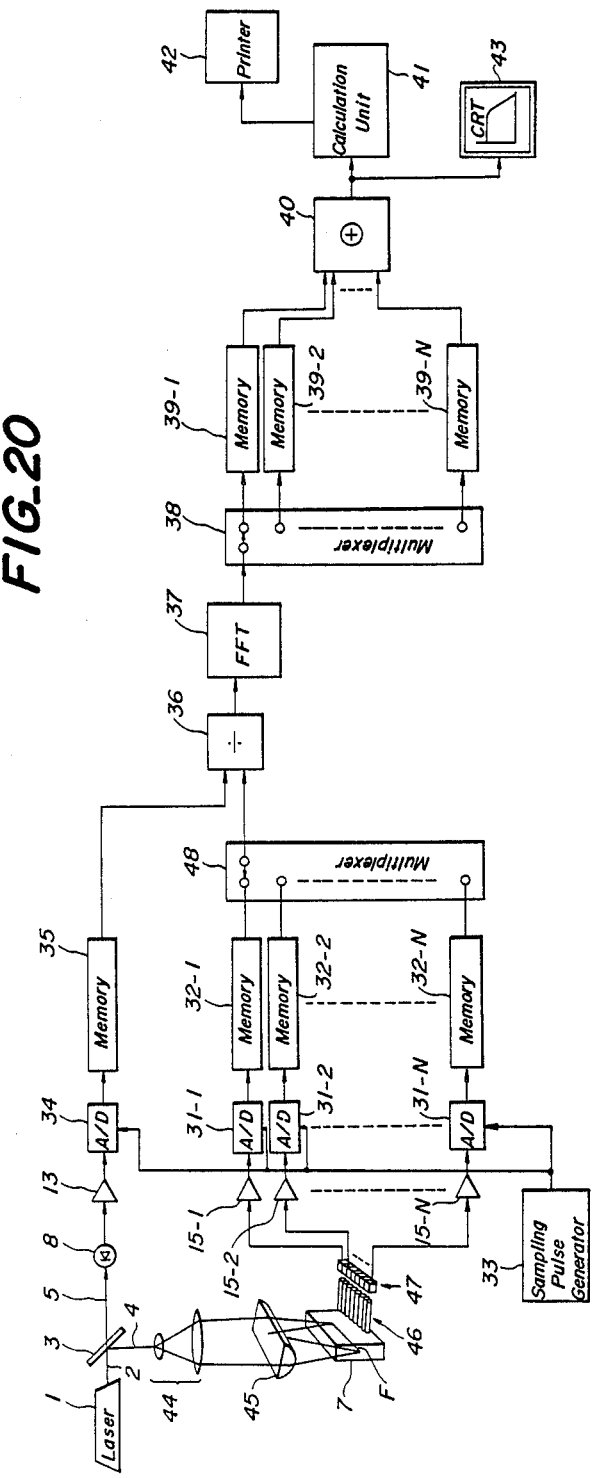

FIG_21
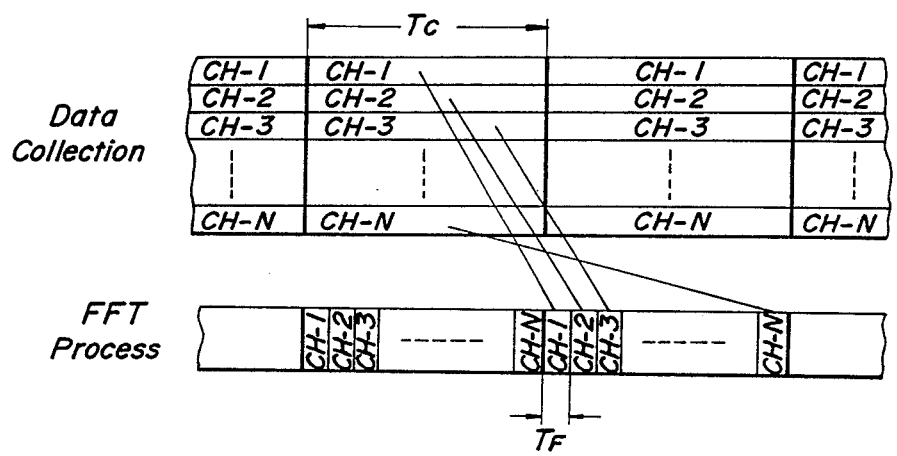

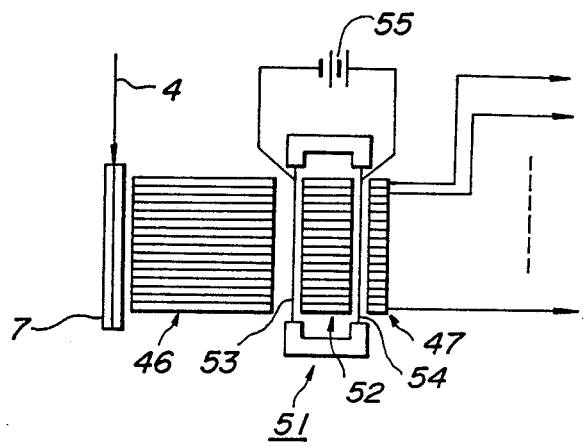
FIG_25
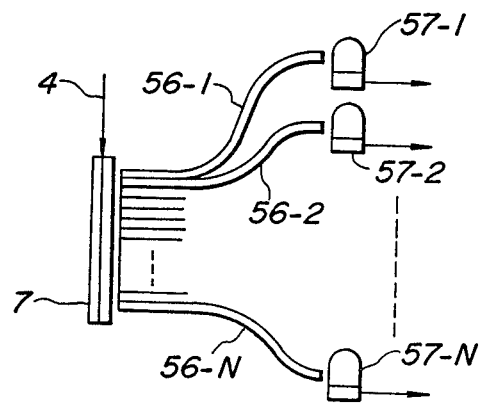
FIG_26
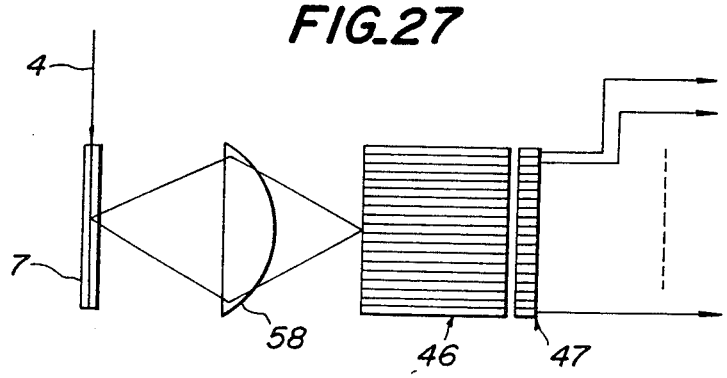
FIG_27

FIG_35
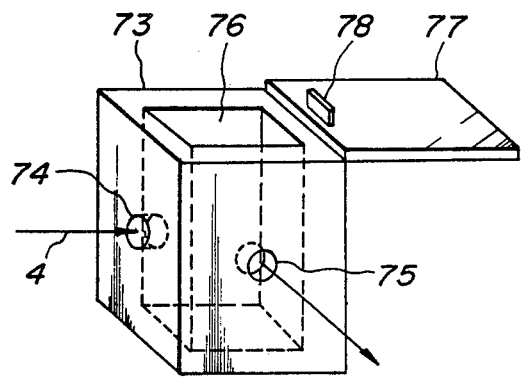
FIG_36
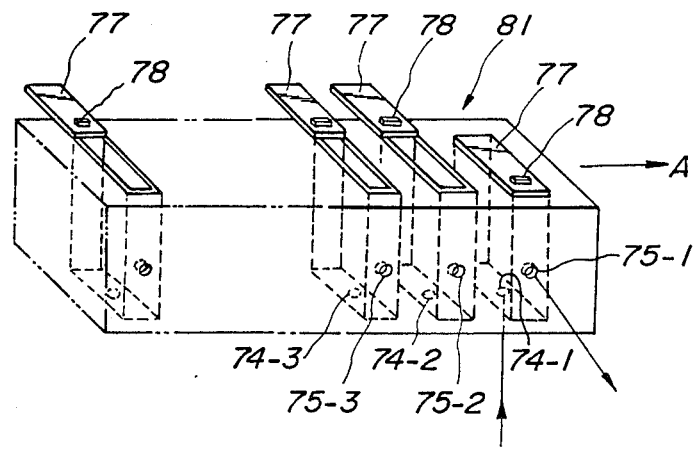

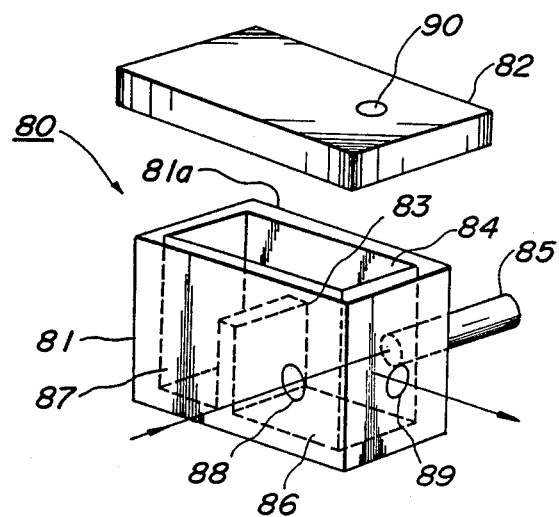
FIG_38
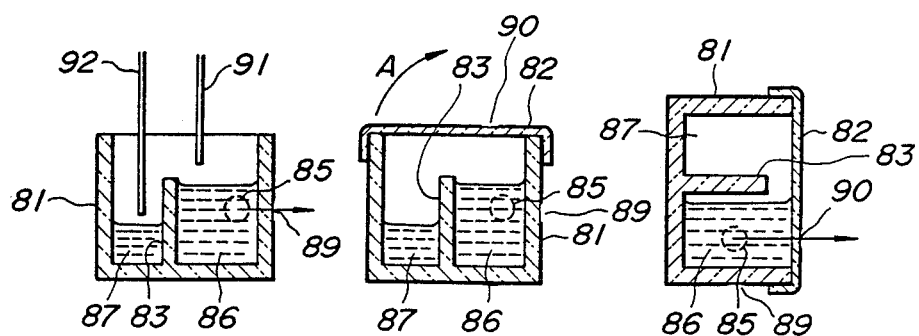
FIG_39A  FIG_39B  FIG_39C

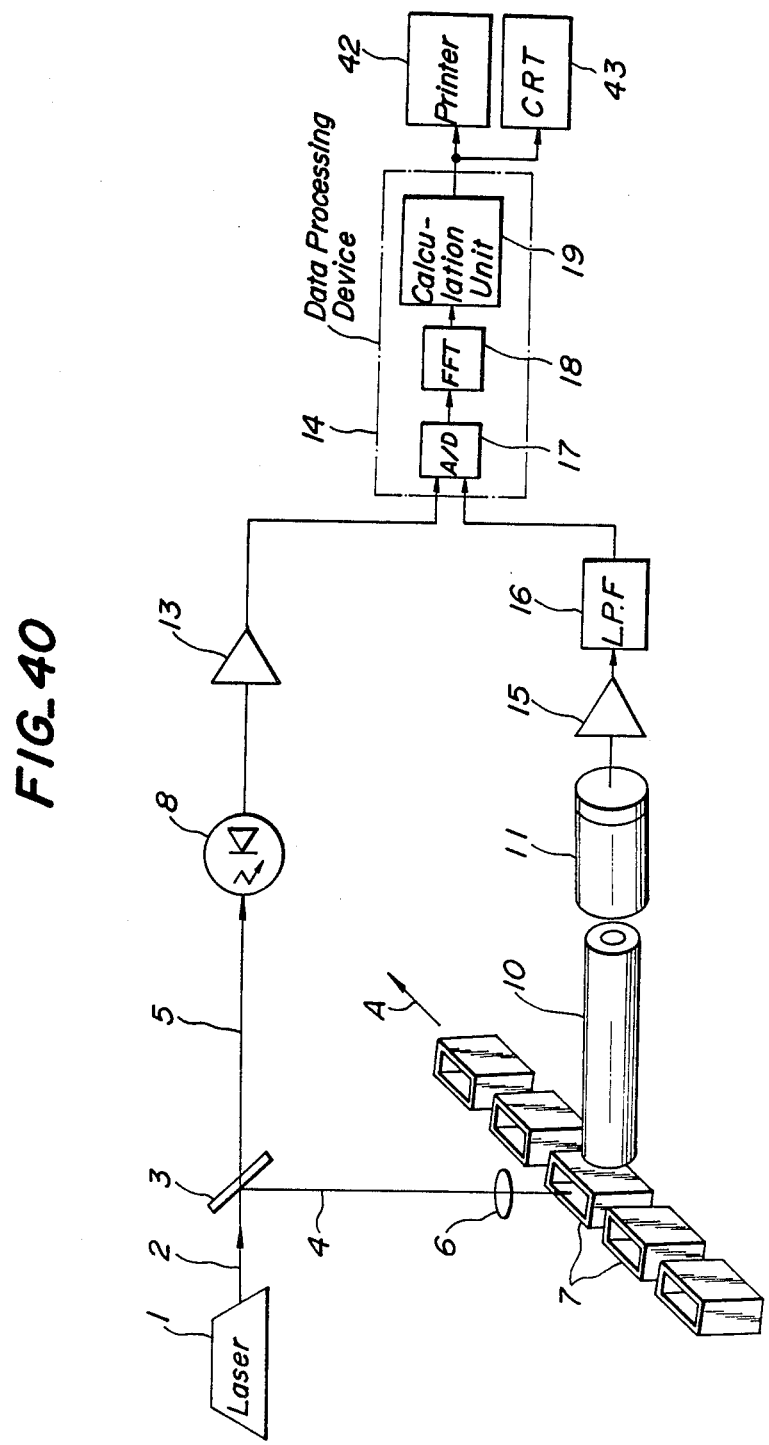

FIG_42A
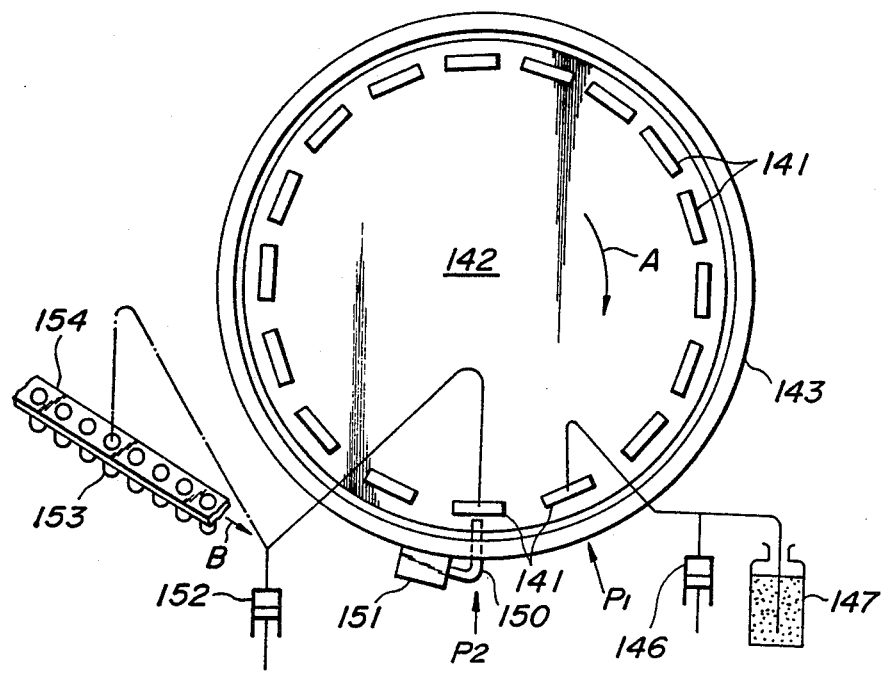
FIG_42B
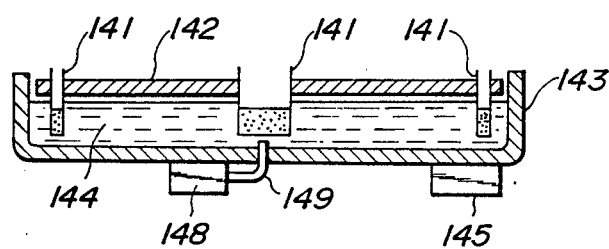

FIG_43A
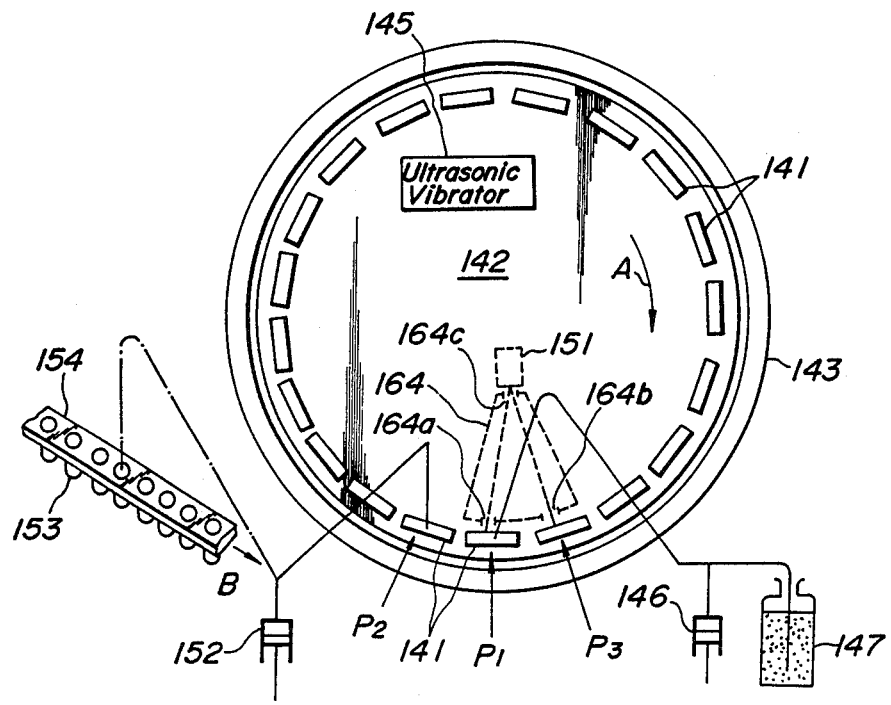
FIG_43B
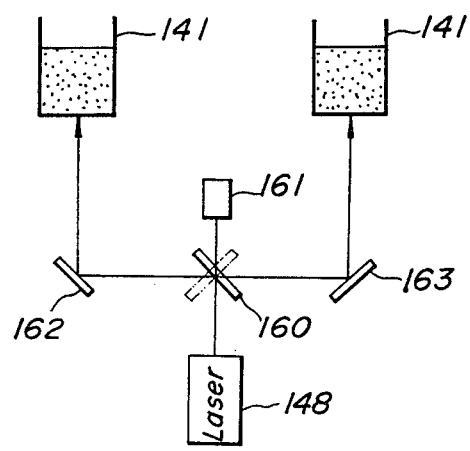

METHOD AND APPARATUS FOR MEASURING IMMUNOLOGICAL REACTION WITH THE AID OF FLUCTUATION IN INTENSITY OF SCATTERED LIGHT

BACKGROUND OF THE INVENTION

1. Field of the Invention

The present invention relates to a method and apparatus for measuring an immunological antigen-antibody reaction with the aid of fluctuation in intensity of light scattered by fine particles suspended in a reaction liquid, and also relates to a measuring cell for use in such method and apparatus.

2. Related Art Statement

There has been developed an immunological analysis for measuring immune substances, hormones, medicines, and various components such as immune regulators faintly contained in living bodies by utilizing a specific immunological reaction. The immunological analysis may be roughly classified into labeling immunological analysis in which enzymes and isotopes are used as an indicator substance, and nonlabeling immunological analysis in which antigen-antibody complexes are directly measured.

In the former labeling immunological analysis, there have been widely known radio immuno assay (RIA), enzyme immuno assay (EIA) and fluorescent immuno assay (FIA). These assays have an advantage in that a high sensitivity can be attained, but also have a drawback in that handling of isotopes and waste liquid is difficult, and measuring periods are liable to be long. Further, since the labeling reagents are expensive, the test cost per sample, i.e. running cost is liable to be high.

In the latter non-labeling immunological analysis, there have been developed immuno electrophoresis, immuno diffusion and sedimentation. These methods are rather simple, but do not have sufficiently high sensitivity, quantitativeness and reproducibility necessary for precise measurement.

In "Immuno chemistry", vol. 12, No. 4 (1975), pages 349 to 351, there has been proposed an immunological analysis in which antigen or antibody bound on surfaces of fine particles are reacted with antibody or antigen contained in a test liquid, and an average diffusion constant which is an indicia of the Brownian motion of aggregates composed of agglutinated particles is measured from a variation in a spectral width of laser light scattered from a particle suspension. This method has merit in that no reagent is used. However, since the spread of the spectrum due to the Doppler effect owing to the Brownian motion of aggregates is detected by a spectrometer, the apparatus is liable to be large in size and expensive in cost. Further, error might be induced when the spectrometer is driven mechanically, so that precision and reproducibility are degraded. Moreover, in this known method, since merely the average diffusion constant is measured from the spectral width, an amount of available information about the antigen-antibody reaction is limited.

SUMMARY OF THE INVENTION

The present invention has for its object to provide a novel and useful method for measuring an antigen-antibody reaction, in which method it is not necessary to use expensive reagents, and an expensive and large spectrometer and the measurement can be carried out reproducibly at a high precision.

It is another object of the invention to provide an immunological reaction measuring method in which the measurement can be performed automatically within a relatively short time period.

It is still another object of the invention to provide an immunological reaction measuring method in which a very small concentration of antigen or antibody contained in a test sample can be measured accurately.

According to the invention, a method of measuring immunological reaction comprises the steps of:

projecting radiation to a reaction liquid containing at least antigen and antibody;

detecting radiation scattered by particulate substances in the reaction liquid;

deriving a plurality of power spectrum densities of fluctuation in intensity of said scattered radiation;

deriving a mean power spectrum density in accordance with said plurality of power spectrum densities; and measuring antigen-antibody reaction on the basis of said mean power spectrum density.

The present invention also relates to an apparatus for carrying out the method of measuring the immunological reaction with the aid of a fluctuation in intensity of light scattered by particles.

According to the invention, an apparatus for measuring immunological reaction comprises light source means for emitting a light flux;

cell means for containing an antigen-antibody reaction liquid;

optical means for projecting the light flux emitted from the light source means into said cell means;

photodetector means for receiving light scattered by particulate substances included in said antigen-antibody reaction liquid to produce an output electrical signal;

means for receiving the output electrical signal supplied from the photodetector means and deriving a plurality of power spectrum densities of fluctuation in intensity of scattered light;

means for deriving a mean power spectrum density in accordance with said plurality of power spectrum densities; and means for measuring the antigen-antibody reaction on the basis of the mean power spectrum density.

The present invention is based on the following recognition. The intensity of light scattered by aggregates of particles produced by an antigen-antibody reaction is fluctuated due to light interference, and a power spectrum density of the fluctuation in intensity of scattered light depends upon the shape and size of aggregates of particles. Therefore, by detecting the power spectrum density of intensity fluctuation, it is possible to derive a large amount of useful information about an immunological reaction such as existence of an antigen-antibody reaction, quantitative information of the antigen or antibody, and agglutinated condition of aggregates of particles (diameter of aggregates) due to antigen-antibody reaction. According to the invention, since the fluctuation in intensity of scattered light can be measured simply by detecting the scattered light by means of a photodetector, it is no longer necessary to use any expensive reagent. Moreover, since spectrum analysis of the scattered light is not effected, it is not at all necessary to provide a large and expensive spectrometer.

In a preferred embodiment of the invention, the scattered light is detected in a homodyne manner and a ratio of relaxation frequencies of the power spectrum density of fluctuation in intensity of scattered light before and after the antigen-antibody reaction is derived to measure the antigen-antibody reaction. This is based on the fact that the relaxation frequency is intimately related to size of aggregates of agglutinated particles.

In another preferred embodiment of the invention, a ratio of integrated values of the power spectrum density in a lower frequency range before and after the antigen-antibody reaction is measured. This is based on the fact that the integrated value of the power spectrum density of fluctuation in intensity of scattered light in the lower frequency range is closely related to size of aggregates of particles.

According to the invention the fluctuation in intensity of light scattered by agglutinated particles is detected on the basis of the power spectrum density, and therefore it is not necessary to use expensive reagents and a spectrometer and further a large amount of useful information about the antigen-antibody reaction can be obtained in a very short time period at high sensitivity and reproducibility even if the concentration of antigen or antibody to be tested is very small.

BRIEF DESCRIPTION OF THE DRAWINGS

FIG. 1 is a schematic view showing an embodiment of the immunological measuring apparatus according to the invention;

FIG. 2 is a schematic view illustrating a construction of a collimator shown in FIG. 1;

FIG. 3 is a schematic view depicting an arrangement of major parts of another embodiment of the immunological measuring apparatus according to the invention;

FIGS. 4 and 5 are graphs showing power spectrum density curves for particles having diameters of 0.188 $\mu$m and 0.305 $\mu$m, respectively;

FIG. 6 is a graph representing a relation between a particle diameter and a relaxation frequency of power spectrum density;

FIGS. 7 and 8 are graphs showing power spectrum density curves for particle concentrations of 0.1% by weight and 0.09% by weight, respectively;

FIG. 9 is a graph representing a relation between the particle concentration and relative fluctuation;

FIGS. 10 and 11 are graphs showing power spectrum density curves before and after the antigen-antibody reaction for antigen concentrations of $10^{-4}$ g/ml and $10^{-9}$ g/ml, respectively;

FIG. 12 is a graph representing a relation between the antigen concentration and ratio of relaxation frequencies;

FIG. 13 is a graph showing a relation between the antigen concentration and ratio of relative fluctuations;

FIGS. 14 and 15 are schematic plan and perspective views showing an embodiment of the immunological analyzer according to the invention in which particles are agitated by ultrasonic wave;

FIG. 16 is a schematic plan view depicting an alternative of the analyzer shown in FIG. 14;

FIG. 17 is a schematic perspective view illustrating still another alternative of the analyzer shown in FIG. 14;

FIG. 18 is a schematic view showing another embodiment of the analyzer according to the invention;

FIGS. 19A and 19B are graphs explaining the operation of the analyzer shown in FIG. 18;

FIG. 20 is a schematic view showing still another embodiment of the analyzer according to the invention;

FIG. 21 is a timing chart for explaining the operation of the analyzer shown in FIG. 20;

FIGS. 25, 26 and 27 are schematic plan views showing another embodiments of the channel construction shown in FIG. 24;

FIG. 35 is a perspective view illustrating a cell box shown in FIG. 34;

FIG. 36 is a perspective view depicting another embodiment of the cell box;

FIG. 38 is a perspective view illustrating a cell shown in FIG. 37;

FIGS. 39A to 39C are cross sectional views for explaining the operation of the analyzer illustrated in FIG. 37;

FIG. 40 is a schematic view showing still another embodiment of the analyzer according to the invention;

FIGS. 42A and 42B are schematic plan and sectional views, respectively depicting another embodiment of the analyzer according to the invention; and FIGS. 43A and 43B are schematic plan and side views, respectively showing still another embodiment of the analyzer according to the invention.

DESCRIPTION OF THE PREFERRED EMBODIMENTS

Figure 22:
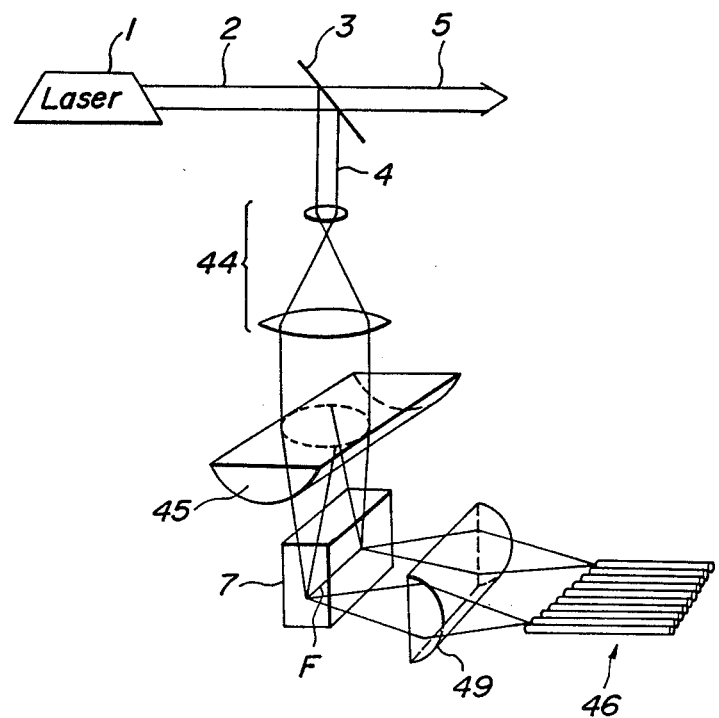
FIGS. 22 and 23 are perspective views illustrating another embodiment of the channel construction shown in FIG. 20.

FIG. 1 is a schematic view showing an embodiment of the immunological reaction measuring analyzer according to the invention. In the present embodiment, a light source for emitting coherent light is constructed by He-Ne gas laser 1 emitting a laser beam having a wavelength of 632.8 nm. The light source emitting the coherent light may be formed by a solid state laser such as a semiconductor laser. A laser light flux 2 emitted from the light source 1 is divided by a beam splitter 3 into light fluxes 4 and 5. The light flux 4 is collected by a condenser lens 6 and is made incident upon a cell 7. The cell 7 is made of transparent quartz. The light flux 5 is made incident upon a photodetector 8 such as a silicon photodiode. Then the photodetector 8 generates a monitor signal representing a variation of the intensity of light emitted from the light source 1.

In the cell 7 is contained an antigen-antibody reaction liquid which is a mixture of a buffer solution, in which fine particles 9 are suspended, and a test sample containing an antigen or antibody to be tested. On outer surfaces of particles 9 are bound antibody or antigen which is specifically reacted with antigen or antibody in the test sample. Therefore, in the cell 7, the antigen-antibody reaction occurs and attractive forces are generated between particles. Then the particles are agglutinated with each other to form aggregates and the Brownian motion of the aggregates is changed in accordance with size and shape of the aggregates.

In the present embodiment, there is provided an ultrasonic vibrating element 21 which is in contact with the cell 7 so that an ultrasonic wave having a frequency of 20 to 40 KHz is applied to the reaction liquid via the wall of cell 7. Then, the particles 9 in the cell 7 are excited by the ultrasonic energy and the probability that antigens and antibodies come in contact with each other is materially increased. Therefore, even if the antigen concentration is extremely low such as $10^{-9}$ g/ml, the antigen-antibody reaction is promoted and is sufficiently effected within a short time. It should be noted that the intensity of ultrasonic energy should be sufficiently large for moving the particles, but should not be higher than a value at which the couplings between the antigens and antibodies might be broken. The application of ultrasonic energy may be interrupted during the measurement. Alternatively, the ultrasonic energy may be applied even during the measurement, because the frequency range of the ultrasonic vibration is far from the frequency component of the fluctuation due to the Brownian motion and thus the ultrasonic energy does not affect the measurement at all. In general, since the cell 7 is very small such as 10 mm (width)×10 mm (height)×1 mm (thickness), it is practically impossible to effect usual agitation. According to the present embodiment, the agitation can be performed effectively by applying the ultrasonic energy to the cell 7 from the exterior, and further the application of the ultrasonic energy does not give any influence upon the measurement.

Light rays scattered by the particles 9 in the cell 7 are made incident upon a photodetector 11 via a collimator 10 having a pair of pin holes. The photodetector 11 is formed by a photomultiplier having a very high sensitivity.

The output monitor signal from the photodetector 8 is supplied via a low noise amplifier 13 to a data processing device 14 to which is also supplied an output signal from the photodetector 11 by means of low noise amplifier 15 and low pass filter 16. The data processing device 14 comprises A/D converter unit 17, fast Fourier transformer (FFT) unit 18 and calculation unit 19 and processes the signals as will be explained hereinafter to derive a measurement result of the antigen-antibody reaction. The measurement result is displayed by a display device 20.

The output signal from the photodetector 11 represents an intensity of the scattered light emanating from the measuring cell 7 and is normalized by the monitor signal supplied from the photodetector 8 and averaged for a short time period. Then any fluctuation due to the variation of intensity of the laser light flux 2 emitted from the light source 1 can be removed. Next, the power spectrum density of fluctuation in intensity of scattered light is detected, and the agglutination condition of particles 9 in the cell 7, and thus the proceeding of the antigen-antibody reaction, are measured.

FIG. 2 is a schematic view illustrating a detailed construction of the collimator 10 shown in FIG. 1. The collimator 10 comprises a tube 10a which is made of opaque material so as to remove the influence of external light. Further, an inner wall of the tube 10a is provided with an anti-reflecting coating. On both ends of the tube 10a there are provided pin holes 10b and 10c. Now it is assumed that radii of the pin holes 10b and 10c are $a_1$ and $a_2$, respectively, a distance between the pin holes is L, a refractive index of a medium inside the tube 10a is n, and a wavelength of the light is λ, then the collimator 10 is formed to satisfy the following equation (1).

$$L \cong \frac{4n \cdot a_1 \cdot a_2}{\lambda} \tag{1}$$

According to the invention, the power spectrum density of fluctuation in intensity of scattered light is detected. The power spectrum density can be represented by a term of fluctuation due to interference of light which is caused by particles which are making random motion, and a term of fluctuation of the number of particles which enter into and go out of a scattering volume. The first term fluctuation due to the interference is observed as a spatial fluctuation of a speckle pattern. If this spatial fluctuation is detected by a photodetector having a wide light receiving area, a spatial average over the area of the light receiving surface is effected and therefore, only a small fluctuation can be detected. In the present embodiment, the field of view of the photodetector 11 is limited by means of collimator 10 having the pin holes, so that the fluctuation can be detected at a very high sensitivity. The above equation (1) can be satisfied by using the collimator 10 with the pin holes having diameter of 0.3 mm and separated from each other by 30 cm, while the medium inside the collimator is air having a refractive index n=1.

In the embodiment shown in FIG. 1, the direction of the light flux 4 impinging upon the cell 7 is made at right angles with respect to the optical axis of the collimator 10, so that the incident light flux is not directly introduced into the photodetector 11. This is called the homodyne detection method. According to the invention, it is also possible to use the heterodyne detection method in which a part of the incident light flux is made incident upon the photodetector 11. That is to say, in the heterodyne detection, an inclination angle θ between the incident light flux 4 and the optical axis of the collimator 10 shown in FIG. 3 is set to zero. According to the invention, the inclination angle θ may be determined at will. In the homodyne arrangement shown in FIG. 1, the output signal from the photodetector 11 is proportional to a mean square value $\overline{E_s^2}$, where $E_s$ is an amplitude of electric field of scattered light. In the heterodyne arrangement, the output signal from the photodetector 11 is expressed as follows:

$$\overline{(E_e+E_s)^2} = \overline{E_e^2} + \overline{2E_e \cdot E_s} + \overline{E_s^2}$$

wherein $E_e$ is an intensity of electric field of the direct incident light. $E_e$ does not fluctuate at all or fluctuates only slowly as compared with the fluctuation of scattered light, and the last two terms fluctuate. Since the scattered light intensity is much weaker than the incident light, $2\overline{E_e \cdot E_s} >> \overline{E_s^2}$. That is to say, in the heterodyne method, it is possible to derive an output signal which is substantially proportional to the amplitude $\overline{E_s}$ of the electric field of scattered light.

Further, it should be noted that the collimator 10 is not limited to the embodiment explained above, but may be constructed in various forms as long as the field of view of the photodetector 11 can be confined smaller than one speckle pattern.

Now the signal processing will be explained. The output signal from the photodetector 11 is supplied to the data processing device 14 via the low pass filter 16 and is processed therein together with the output monitor signal from the photodetector 8 to derive the power spectrum density of fluctuation in intensity of scattered light. A power spectrum density S(f) of the stationary stochastic process x(t) may be expressed as follows.

$$S(f) = \lim_{T \to \infty} \frac{1}{2T} < \left| \int_{-T}^{T} x(t) e^{-2\pi i f t} dt \right|^2 > \quad (2)$$

The power spectrum density of fluctuation in intensity of scattered light means an amount of the power of the intensity or amplitude of scattered light in a frequency range from f to f+Δf, and is generally defined by the following equation.

$$\lim_{\Delta f \to 0} \frac{\psi^2 x(f,\Delta f)}{\Delta f}$$

wherein $\psi^2 x(f,\Delta f)$ is a mean square value in a time series between f and f+Δf. The mean square value is given by the following equation.

$$< \left| \int_{-T}^{T} x(t) e^{-2\pi i f t} dt \right|^2 >$$

Therefore, the power spectrum density of fluctuation in intensity of scattered light can be expressed by the above mentioned equation (2).

In the present embodiment, the power spectrum density is normalized by the monitor signal supplied from the photodetector 8, and therefore the dimension of the power spectrum density may be expressed by 1/Hz.

On the basis of this equation (2), the Fourier transformation is performed to calculate the power spectrum density. The output signal from the photodetector 11 is amplified by the low noise amplifier 15 in such a manner that signal values can cover a wide range of A/D conversion quantum levels, and data thus quantized is calculated by a microprocessor to derive the power spectrum density. From the power spectrum density, the condition of the immunological reaction is measured as will be explained later and is displayed numerically on the display unit 20.

FIGS. 4 and 5 are graphs showing power spectrum density curves which are obtained when test liquids having dispersed polystyrene latex particles having diameters 0.188 μm and 0.305 μm, respectively are introduced in the cell 7 shown in FIG. 1. In these graphs, the normalized power spectrum density (1/Hz) is denoted on the ordinates. There are obtained Lorentz's type power spectrum density curves. This reflects the interference component of the power spectrum density of fluctuation in intensity of scattered light. From these curves, one can recognize that a relaxation frequency of the power spectrum density is inversely proportional to the diameter of the particle. As explained above, the fluctuation in intensity of scattered light is a sum of the component due to the interference of coherent light and the component due to the variation in the number of particles within the scattering volume. In the present embodiment, the component due to the interference is mainly detected. Then the relaxation frequency of the power spectrum density which is defined by a frequency at a shoulder of the power spectrum density curve is equal to the inverse of a time required for aggregates to move over the distance equal to the wavelength. When the diameter of aggregates of particles is increased, the travelling time becomes longer and thus the relaxation frequency becomes lower.

FIG. 6 is a graph showing a relation between the particle size denoted on the abscissa and the relaxation frequency denoted on the ordinate in the homodyne detection. Both the coordinates are denoted by logscale. For the particles having diameter of 0.0915 μm the relaxation frequency is about 400 Hz, for particles of diameter of 0.188 μm the relaxation frequency is about 200 Hz, and for particles of diameter of 0.305 μm, the relaxation frequency of about 100 Hz is observed. As clearly understood from the graph shown in FIG. 6, the relaxation frequency is inversely proportional to particle diameter and therefore, by detecting the variation in the relaxation frequency during the immunological reaction, it is possible to measure an existence of agglutination of particles due to the antigen-antibody reaction and degree of the agglutination. That is to say, when the antigen-antibody reaction is effected in the cell 7, fine particles are agglutinated with each other to form larger aggregates and then the relaxation frequency becomes lower.

FIGS. 7 and 8 are graphs showing the power spectrum density curves which are obtained when polystyrene latex particles having diameter of 0.3 μm are suspended in a buffer solution by concentrations of 0.1% by weight and 0.09% by weight, respectively. Both curves are of the Lorentz type. As explained above, the fluctuation in intensity of scattered light is a sum of the interference component due to the Brownian motion of particles and the non-interference component due to the variation in the number of particles in the scattering volume. When the number of particles in the scattering volume is small, the interference component becomes smaller and compatible with the non-interference component. Then, components other than the fluctuation in intensity of scattered light due to the Brownian motion of particles may be detected and the antigen-antibody reaction can not be measured precisely. Therefore, the concentration of particles should be determined in such a manner that the incident light is sufficiently strong within the scattering volume and the interference component becomes larger than the non-interference component.

FIG. 9 is a graph showing the relation between the number of particles in 1 mm³ and a relative fluctuation $<\delta I^2>/<I>^2$. When a diameter of a scattering body is constant, the relative fluctuation also becomes constant over a relatively wide range of the particle concentration. This can be experimentally confirmed by the curve shown in FIG. 9.

FIGS. 10 and 11 are graphs illustrating power spectrum density curves before and after (fifteen minutes) the antigen-antibody reaction. These curves were obtained by dispersing polystyrene latex particles having diameter of 0.3 μm and having anti-immuno globulin G (anti-IgG) bound on their surfaces in a buffer solution having PH 7 adjusted by Tris-HCl and immuno globulin G is introduced in the suspension by the concentration of $10^{-4}$ g/ml and $10^{-9}$ g/ml, respectively. As shown in FIG. 10, in case of the antigen concentration of $10^{-4}$ g/ml, prior to the reaction, the relaxation frequency was about 50 Hz and after fifteen minutes the relaxation frequency was decreased to 10 Hz. Contrary to this, in case of the antigen concentration of $10^{-9}$ g/ml, the relaxation frequency before the reaction was about 95 Hz and decreased to about 40 Hz after reaction. Therefore, when a ratio F of the relaxation frequency before and after the reaction, the following table is obtained.

$$F = \frac{\text{Relaxation Frequency before Reaction}}{\text{Relaxation Frequency after Reaction}}$$

The relation between the ratio F and antigen concentration is represented by a curve shown in FIG. 12. In FIG. 12, the abscissae denotes the concentration of antigen and the ordinate represents the ratio F of the relaxation frequency. In this manner, according to the invention the antigen concentration can be measured by deriving the ratio F of the relaxation frequency before and after the reaction.

From the graphs shown in FIGS. 10 and 11, it can be further recognized that a ratio R of relative fluctuations before and after the antigen-antibody reaction is related to the concentration of antigen. Next, this will be explained in detail. In FIG. 1, the electrical output signal from the photodetector 11 receiving the scattered light is passed through a low pass filter having the following transfer function H(f).

$$H(f) = \frac{f_c}{f + if_c} \quad (3)$$

wherein $f_c$ is a cut-off frequency of the low pass filter which is sufficiently lower than the relaxation frequency $f_r$. Then, a variance of the fluctuation in an output electrical current I from the low pass filter can be expressed as follows.

$$<\delta I^2> = K^2<N> + K^2<N>^2 f_c/f_r \quad (4)$$

where K is a constant and $<N>$ is a mean number of particles in the scattering volume. Therefore, a relative fluctuation in the output current of the low pass filter can be represented by the following equation (5).

$$\frac{<\delta I^2>}{<I>^2} = \gamma \frac{f_c}{f_r} + \frac{1}{<N>} \quad (5)$$

wherein $\gamma$ is a proportionality constant. Since it can be assumed that the number of particles in the scattering volume is sufficiently large, the equation (5) can be rewritten as follows.

$$\frac{<\delta I^2>}{<I>^2} = \gamma \frac{f_c}{f_r} \quad (6)$$

This equation shows that the relative fluctuation can be calculated by deriving the relaxation frequency $f_r$ from the power spectrum density curve. Then the ratio R of relative fluctuation can be represented by the following equation (7).

$$R = \frac{\text{Relative Fluctuation after Reaction}}{\text{Relative Fluctuation before Reaction}} \quad (7)$$

FIG. 13 is a graph showing the relation between the ratio R of relative fluctuation and antigen concentration. From this graph it can be clearly understood that an unknown concentration of antigen can be measured by deriving the ratio R of relative fluctuations before and after the antigen-antibody reaction. That is to say, prior to the actual measurement the ratio R of relative fluctuation is detected by using standard samples having known antigen concentrations to form a calibration curve similar to the curve shown in FIG. 13. Then a ratio R of relative fluctuation is detected for a sample and unknown antigen concentration of the sample is measured from the calibration curve.

The ratio R of relative fluctuation defined by the equation (7) can be derived as a ratio of integrated values of the power spectrum density curve in a lower frequency range. That is to say, the ratio R of relative fluctuation can be also detected in accordance with the following equation (8).

$$R = \frac{\text{Integrated Value of Power Spectrum Density after Reaction } (B)}{\text{Integrated Value of Power Spectrum Density before Reaction } (A)} \quad (8)$$

As shown in FIGS. 10 and 11 the integrated values A and B of the power spectrum density before and after the reaction are obtained by integrating the power spectrum density from $10^{-1}$ Hz to $10^1$ Hz. Therefore, the low pass filter is composed to pass this frequency range.

In FIGS. 10 and 11, the ratio R of relative fluctuation is derived as a ratio between the integrated values A and B of the power spectrum density in the lower frequency range. According to the invention, it is also possible to derive the ratio R of relative fluctuation at a certain frequency in the low frequency range, e.g. $10^0$ Hz. In such a case, a digital filter may be used instead of the fast Fourier transformer and thus the whole construction can be made very simple and the processing time becomes very short.

In case that size of aggregates of particles is relatively uniform, the power spectrum density becomes the Lorentz type and decreases inversely proportional to a square of frequency beyond the relaxation frequency. However, when the aggregate size is distributed, there may be observed a superposition of a plurality of Lorentz type power spectrum density curves having different relaxation frequencies and therefore, the power spectrum density does not decrease inversely proportional to the frequency. This means that a distribution of aggregate size can be known from a configuration of the power spectrum density curve in a higher frequency range. Such data could never be obtained by known analyzing methods and is very useful for analyzing the antigen-antibody reaction.

FIG. 14 is a schematic plan view showing an embodiment of the immunological analyzer according to the invention, in which the reaction liquid can be agitated by ultrasonic energy. In the present embodiment, a plurality of cuvettes 23 are arranged on a turntable 22 along its periphery. The turntable 22 is rotated intermittently in a direction indicated by an arrow A. At a position a, a given amount of a sample containing antigens to be measured is delivered into a cuvette 23. At a position b, a first photometry is effected and then at a position c, a given amount of a reagent containing particles having antibodies bound thereon is delivered into the relevant cuvette. After a suitable reaction time has passed, at a position d, a second photometry is performed to detect a light flux scattered by agglutinated particles. In the present embodiment, the cuvette 23 serves as the photometric cell 7 shown in FIG. 9. After the measurement, the cuvette 23 is washed at a position e. According to present embodiment, the ultrasonic energy is applied to the reaction liquid contained in the cuvette 23, while the cuvette is transported from the position c to the position d. Therefore, the particles in the reaction liquid are vibrated and thus the antigen-antibody reaction is promoted. This results in that the rotating speed of the turntable 22 can be increased.

As illustrated in FIG. 15, the turntable 22 is rotated by a motor 24 and the cuvettes 23 are immersed in a liquid 27 contained in a thermostat 25. On a bottom surface of the thermostat 25 is secured an ultrasonic vibration element 26.

Since the liquid 27 of the thermostat 25 conducts the ultrasonic wave very efficiently, the reaction liquids contained in all the cuvettes are excited by the ultrasonic wave and the agitation can be carried out effectively.

FIG. 16 is a plan view showing another embodiment of the analyzer according to the invention in which the reaction liquid is agitated by the ultrasonic wave. In the present embodiment, a plurality of ultrasonic vibrating elements 26 are provided at positions corresponding to positions at which cuvettes 23 arranged on a turntable 22 are stopped. The ultrasonic vibrating elements 26 are arranged movably in radial directions and are driven by suitable actuators not shown into a first position at which the elements are separated from the cuvettes 23 and into a second position at which the elements are brought into contact with the cuvettes. While the turntable 22 is rotated, the ultrasonic vibrating elements 26 are kept in the first position, and while the turntable is stationary, the elements are driven into the second position. In this manner, according to the present embodiment, the reaction liquids contained in the cuvettes are agitated by ultrasonic energy while the cuvettes are kept stationary at positions between the positions c and d in FIG. 14.

FIG. 17 is a schematic perspective view showing still another embodiment of the analyzer according to the invention in which the reaction liquids are excited by the ultrasonic wave. In the present embodiment, ultrasonic vibrating elements 26 are secured to side walls of cuvettes 23 which are arranged on a turntable (not shown). In order to supply the electric power to the ultrasonic vibrating elements 26, to the element are connected conductive brushes 28 which are slidably contacted with concentric conductive rails 29. By rotating the turntable, the conductive brushes 28 are slidably moved over the rails 29 which are connected to an oscillator. It should be noted that the rails 29 may be provided within a range between the positions c and d in FIG. 14. In the present embodiment use must be made of an electrically insulating thermostat liquid or an air-bath type thermostat.

In the embodiments so far explained, the particles in the reaction liquid are moved in a random fashion by means of ultrasonic energy, and thus the antigen-antibody reaction is extremely enhanced. Therefore, the immunological reaction can be measured precisely within a very short time period even if of concentration of antigen or antibody contained in a sample is extremely small.

FIG. 18 is a schematic view showing another embodiment of the immunological analyzer according to the invention. In the present embodiment, elements similar to those shown in FIG. 1 are denoted by the same reference numerals used in FIG. 1. A laser light flux 2 emitted from an He-Ne gas laser 1 is divided into fluxes 4 and 5 by means of a beam splitter 3. The light flux 4 is focussed by a condenser lens 6 onto a transparent cell 7 containing fine particles 9. The light flux 5 is made incident upon a silicon photodiode 8 and its output signal is amplified by a low noise amplifier 13 to generate a monitor signal representing a fluctuation of the laser light source 1.

A light flux scattered by the particles 9 suspended in a reaction liquid contained in the cell 7 is made incident upon a photomultiplier 11 via a collimator 10 having a pair of pin holes. An output signal from the photomultiplier 11 is supplied to a first A/D converter 31 via a low noise amplifier 15. In the first A/D converter 31, during each measuring period the signal from the amplifier 15 is sampled to obtain P digital signals each consisting of M bits. These digital signals are stored in a first memory 32. The sampling operation is controlled by sampling pulses supplied from a sampling pulse generator 33. A capacity of the memory 32 should be equal to or larger than $P \times M$ bits. The monitor signal from the amplifier 13 is also sampled by a second A/D converter 34 under the control of the sampling pulse generator 33 to derive P digital signals each consisting of M bits. These digital signals are stored in a second memory 35. Corresponding digital signals stored in the first and second memories 32 and 35 are then read out and are supplied to a divider 36 to derive a normalized signal in which any fluctuation due to the laser light source 1 has been compensated for. The signal thus derived is supplied to a fast Fourier transformer 37 to obtain a power spectrum density in intensity of the scattered light. According to the present embodiment, the above explained process is repeated several times to derive a plurality of power spectrum densities which are then stored in memories 39-1 to 39-N via a multiplexer 38. Each of the memories 39-1 to 39-N has a storing capacity equal to or larger than $P \times M$ bits. The power spectrum densities stored in the memories 39-1 to 39-N are supplied to a normalizer or averaging circuit 40 to derive a mean power spectrum density which is then supplied to a calculation unit 41. In the calculation unit 41, the calculation is effected in accordance with the mean power spectrum density to derive measuring result such as existence or non-existence of agglutination reaction, and concentration of antigen or antibody contained in a sample. The measuring result thus obtained is supplied to a printer 42. Further, the waveform of mean power spectrum density can be monitored on a cathode ray tube 43.

Since an amount of light scattered by the particles 9 is very small, the power spectrum density obtained by one sampling has a very low S/N as illustrated in FIG. 19A. But according to the present embodiment, the sampling is effected several times to derive a plurality of power spectrum densities and then these power spectrum densities are averaged by the normalizer 40 to obtain the mean power spectrum density. Therefore, S/N of the mean power spectrum density can be increased materially as shown in FIG. 19B. In general, S/N is increased by $\sqrt{N}$ times, when the sampling is carried out by N times. Therefore, if the sampling is performed by a hundred times, S/N can be made higher by ten times. It should be noted that the operation in the calculation unit 41 may be effected in the same manner as that explained above with reference to FIGS. 1 to 13.

FIG. 20 is a schematic view illustrating another embodiment of the immunological analyzer according to the invention. In the present embodiment elements similar to those shown in FIG. 18 are denoted by the same reference numerals used in FIG. 18. A light flux 4 divided by a beam splitter 3 is converted into a parallel beam having a large diameter by means of a beam expander 44 and the parallel beam is made incident upon a transparent cell 7 by means of a cylindrical lens 45 in such a manner that the beam is focused within the cell 7 to form a linear focus line f. The other light flux 5 is made incident upon a silicon photodiode 8 to derive a monitor signal which is then amplified by a low noise amplifier 13.

Light rays scattered by particles suspended in a reaction liquid contained in the cell 7 are made incident via an array of optical fibers 46 upon an array of photodiodes 47. It should be noted that the optical fibers of the array 46 and photodiodes of the array 47 should not be corresponded to each other one by one, but scattered light fluxes transmitted through, for instance, two optical fibers may be received by a single photodiode. In the present embodiment, there are provided N channels for receiving the light fluxes scattered by particles at different locations in the cell 7.

Photoelectrically converted output signals from the photodiode array 47 are parallelly amplified by low noise amplifiers 15-1 to 15-N and then the amplified signals are converted into digital signals by means of A/D converters 31-1 to 31-N under the control of a sampling pulse generator 33. In each A/D converters 31-1 to 31-N, during each measuring period P digital signals each consisting of M bits are sampled and are then stored in first memories 32-1 to 32-N. Therefore, each of the memories 32-1 to 32-N must have a storing capacity equal to or larger than P×M bits.

The monitor signal from the amplifier 13 is also sampled by an A/D converter 34 under the control of the sampling pulse generator 33 to derive P digital signals each consisting of M bits. The digital monitor signals thus derived are then stored in a second memory 35.

The P digital signals stored in the memories 32-1 to 32-N are successively read out and are supplied to a divider 36 via a multiplexer 48. To the divider the digital monitor signal stored in the memory 35 are also supplied to derive normalized output signals from which any fluctuation of a laser light source 1 has been removed. The output signals thus obtained are supplied to a fast Fourier transformer 37 to derive successively power spectrum densities in intensity of scattered light which are then stored in memories 39-1 to 39-N via a multiplexer 38. The remaining operation is the entirely same as that explained above with reference to FIGS. 18 and 19. That is to say, the N power spectrum densities obtained by means of the N channels are averaged by a normalizer 40 to derive a mean power spectrum density having high S/N. In the present embodiment, the S/N can be increased by $\sqrt{N}$ times by providing N channels.

Now the operation of the analyzer will be explained by way of a numerical example. In the present embodiment, data is processed on real time and the waveform of the mean power spectrum density can be monitored on the cathode ray tube 43 on real time.

A sampling rate in the A/D converters 31-1 to 31-N is made higher than the signal frequency more than two times in accordance with the sampling theory. The frequency components of the fluctuation in intensity of the scattered light is lower than several hundred Hertz, and thus the sampling rate is set to 2 KHz. Therefore, a period of the sampling pulse is 500 $\mu$s which is called a cycle time $T_c$. Further, in each measuring period, there are effected 1024 samplings, i.e. P=1024. Then, the measuring period equals to 500 $\mu$s×1024≅500 ms. That is to say, all the data is collected within about 500 ms.

Since the fast Fourier transformer 37 has to process the data at a high speed, it is constructed by hardware. A cycle time of the fast Fourier transformer 37 is assumed to be 200 ns and a four cycle Butterfly operation is to be effected. Then, a single Butterfly requires 800 ns. The number of Butterfly operations required for the fast Fourier transformation of P=1024 points becomes equal to P/2×log$_2$P=512×10=5120. Therefore, a time necessary for the Fourier transformation per channel becomes 800 ns×5120≅4 ms. As illustrated in FIG. 21, if a data collecting cycle time $T_c$ is assumed to be 500 ms, after the data has been collected during 500 ms, but prior to a next data collection, the Fourier transformation which requires the period $T_F$=4 ms per channel is effected for all N channels. In this manner, the real time processing for at least a hundred channels may be performed.

FIG. 22 is a perspective view showing another embodiment of the channel construction for receiving parallelly light rays scattered at different positions on the focus line F. In this embodiment, between the cell 7 and the optical fiber array 46 is arranged an imaging lens 49 which forms an image of the focus line F onto an incident end surface of the optical fiber array 46. In this case, the imaging lens 49 may be formed by a cylindrical lens as illustrated in FIG. 22, because it does not require to have the imaging power in a direction parallel to the focus line F.

Figure 23:
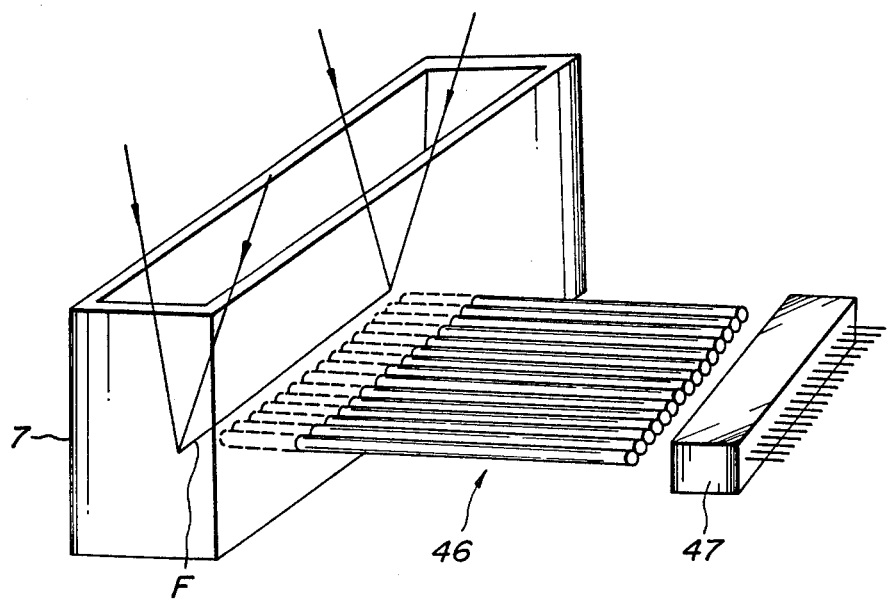

FIG. 23 is a perspective view showing still another embodiment of the channel construction according to the invention. In the present embodiment, an incident end portion of the optical fiber array 46 penetrates into a side wall of the cell 7 in such a manner that the incident end surface of the optical fiber array 46 is situated in the vicinity of the focus line F. Therefore, the resolution of the channel is made much higher and the S/N of the power spectrum density can be increased. It should be noted that at least a part of the optical fibers in the array 46 may be constructed by converging type optical fibers. Then, a distance between the focus line F and the incident end surface of the optical fiber array may be large and thus it is not always necessary to insert the incident end portion of optical fiber array into the cell 7, so that the construction becomes much simpler. It should be further noted that the optical fiber array may be replaced by discrete optical fibers and light rays scattered at different positions of the focus line F may be introduced into photomultipliers via the discrete optical fibers. Moreover, between the cell 7 and the optical fiber array 46 may be arranged a linear channel plate type image intensifier for amplifying the scattered light rays as will be explained later. Such a construction is especially suitable when the scattered light rays are very weak.

In the embodiment shown in FIG. 20, the laser light beam is made incident vertically upon the cell 7 so as to form the focus line F which extends horizontally. According to the invention, it is also possible that the parallel laser light is made incident horizontally upon the cell. Now such an arrangement will be explained hereinbelow.

Figure 24:
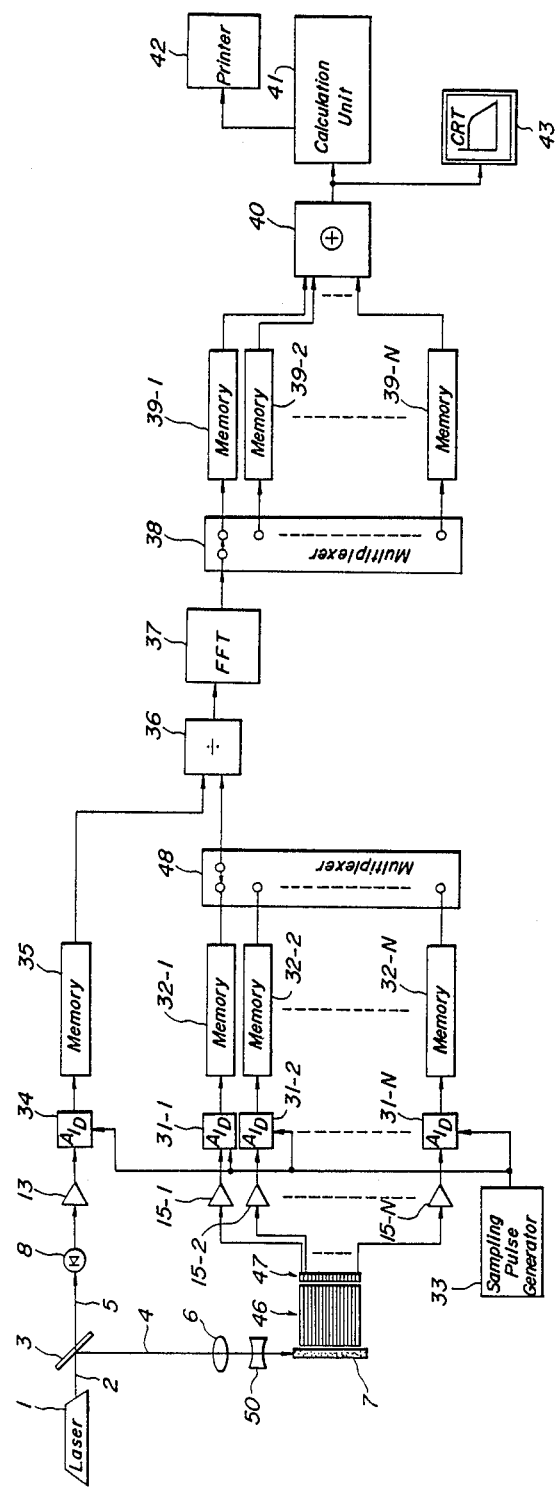
FIG. 24 is a schematic plan view depicting still another embodiment of the analyzer according to the invention.

FIG. 24 is a schematic plan view showing an embodiment of the analyzer according to the invention. In the present embodiment, a laser light flux 4 divided by a beam splitter 3 is collected by a condenser lens 6 and then is converted into a thin parallel beam by means of a collimator lens 50. The parallel beam thus formed is made incident upon a cell 7 horizontally. Light rays scattered at different points in the cell 7 are made incident upon a photodiode array 47 via an optical fiber array 46. The remaining construction of the analyzer of the present embodiment is entirely the same as that shown in FIG. 20 and thus its detailed explanation is omitted. Also in the present embodiment, since a mean power spectrum density is derived, its S/N can be increased materially.

FIG. 25 is a schematic plan view showing another embodiment of the channel construction of the analyzer according to the invention. In this embodiment, a linear multichannel-type image intensifier 51 is arranged between the optical fiber array 46 and photodiode array 47 so as to amplify the weak scattered light. The image intensifier 51 comprises a photocathode 53 arranged opposite to the optical fiber array 46, a fluorescent plate 54 arranged opposite to the photodiode 47, a linear multi-channel plate 52 arranged between the photocathode 53 and fluorescent plate 54, and a power supply source 55 connected across the photocathode and fluorescent plate. Since the image intensifier has a very large amplification factor, the very weak scattered light can be amplified to obtain a power spectrum density having a high S/N.

FIG. 26 is a schematic plan view illustrating another embodiment of the channel construction according to the invention. In the present embodiment, light rays scattered at different points in the cell 7 are made incident upon a plurality of photomultipliers 57-1 to 57-N by means of a plurality of discrete optical fibers 56-1 to 56-N. Since the photomultipliers 57-1 to 57-N have the very high sensitivity, the weak scattered light rays can be detected effectively.

FIG. 27 is a schematic plan view showing still another embodiment of the channel construction according to the invention. In the present embodiment, between the cell 7 and the optical fiber array 46 is arranged an imaging lens 58 which forms an image of a part of plane within the cell along which the parallel light beam is made incident. In this case, the imaging lens 58 may not have the imaging faculty in a direction perpendicular to the plane of the drawing, and thus it may be formed by a cylindrical lens.

Figure 28:
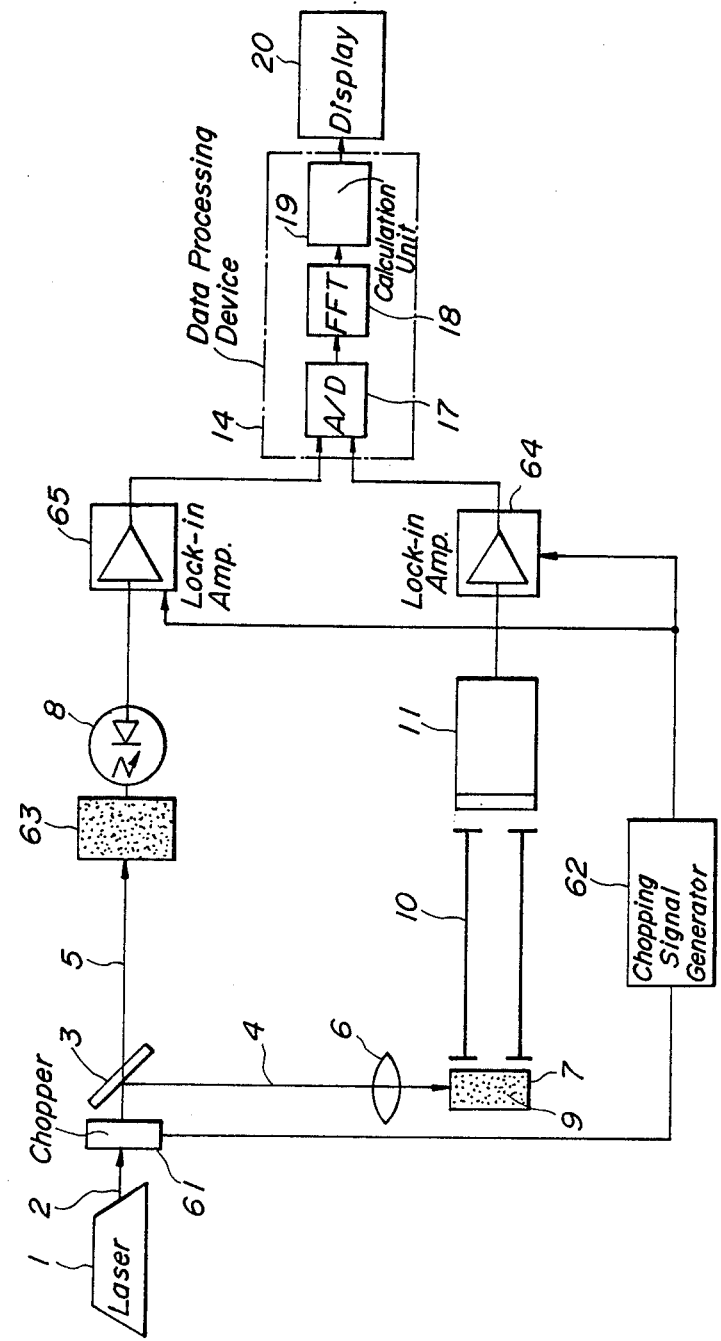
FIG. 28 is a schematic view illustrating still another embodiment of the analyzer according to the invention.

FIG. 28 is a schematic view illustrating still another embodiment of the analyzer according to the invention. In the present embodiment, elements similar to those shown in FIG. 1 are denoted by the same reference numerals as those used in FIG. 1. In the present embodiment, a laser light beam 2 emitted from a laser light source 1 is chopped by a chopper 61 under the control of a chopping signal generator 62, and the chopped laser beam is separated by a beam splitter 3 into chopped light fluxes 4 and 5. The chopping frequency should be set to a value higher than 1 KHz which does not interfere with the frequency of the fluctuation. The light flux 4 is made incident upon a transparent cell 7 via a condenser lens 6 and a light flux scattered by particles 9 is received by a photomultiplier 11 via a collimator 10 having a pair of pin holes. The light flux 5 is made incident upon a transparent reference cell 63 containing a standard sample, e.g. a buffer solution including particles. Then a light flux scattered from the reference cell 63 is made incident upon a silicon photodiode 8. Output signals from the photomultiplier 11 and photodiode 8 are supplied to lock-in amplifiers 64 and 65, respectively which are driven by control signals supplied from the chopping signal generator 62 in synchronism with the chopper 61. In this manner, according to the invention, it is possible to remove the influence of background noise and noise due to drift of a sample. Therefore, the power spectrum density having high S/N can be derived and the measuring accuracy and reliability can be improved materially.

Figure 29:
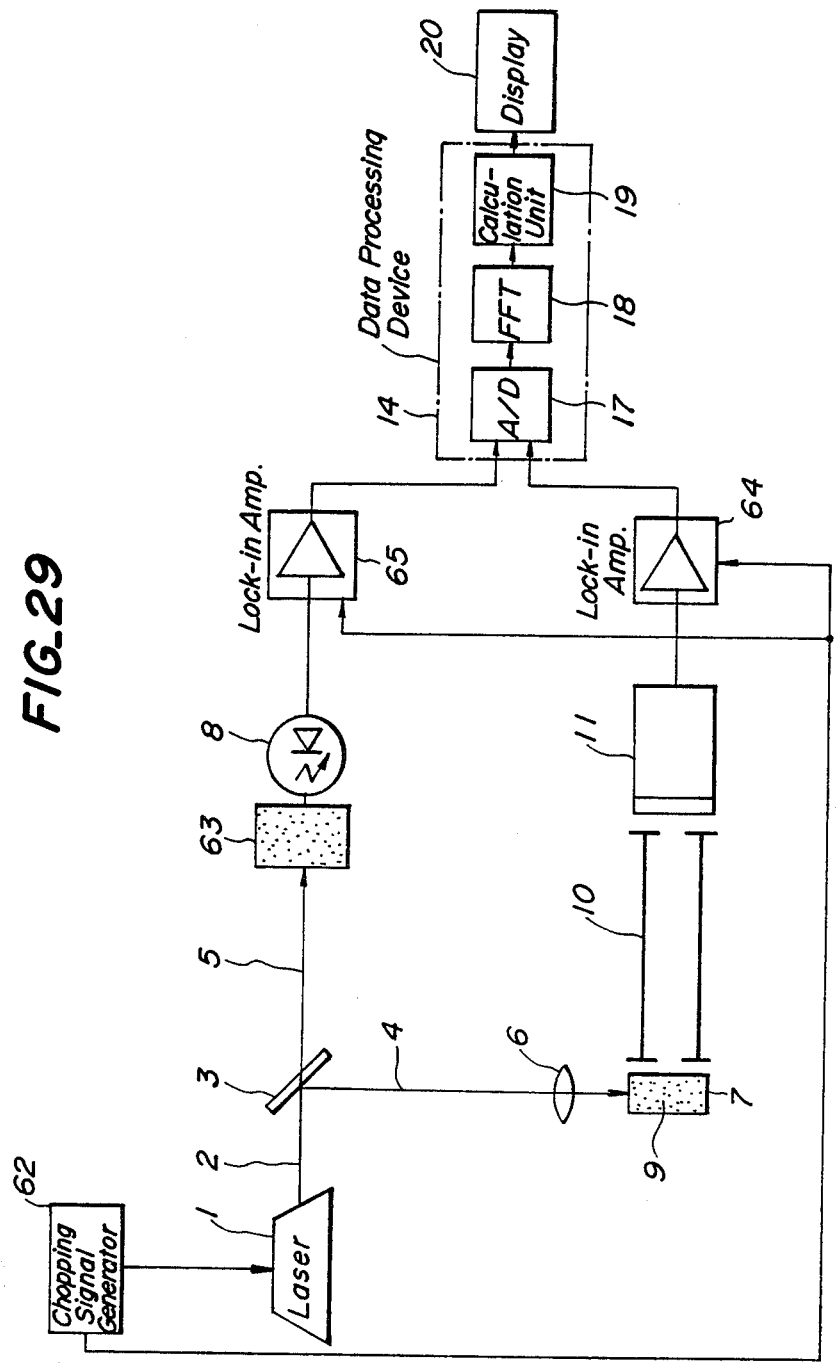
FIGS. 29 and 30 are schematic views showing two modifications of the analyzer shown in FIG. 28.

FIG. 29 is a schematic view showing a modification of the embodiment shown in FIG. 28. In the present embodiment, the chopped laser beam is obtained by directly modulating the laser light source 1 by means of the chopping signal generator 62. The remaining construction is the entirely same as that shown in FIG. 28.

Figure 30:
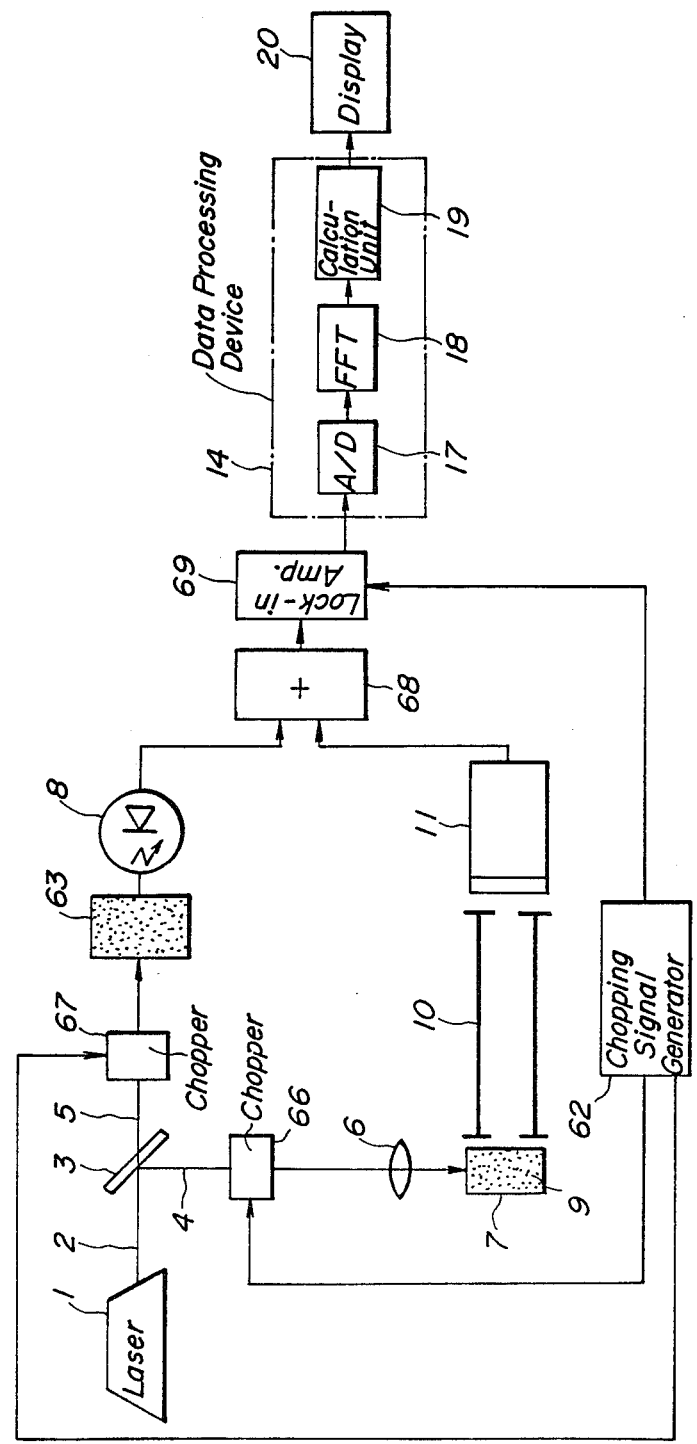

FIG. 30 is a schematic view depicting still another embodiment of the analyzer according to the invention. In the present embodiment a laser beam emitted from a laser light source 1 is divided into fluxes 4 and 5 by means of a beam splitter 3. Then the divided light fluxes 4 and 5 are chopped by means of choppers 66 and 67, respectively under the control of a chopping signal generator 62. The chopped light flux 4 is made incident upon a cell 7 by means of a condenser lens 6 and the chopped light flux 5 is made incident upon a reference cell 63.

Figure 31A:
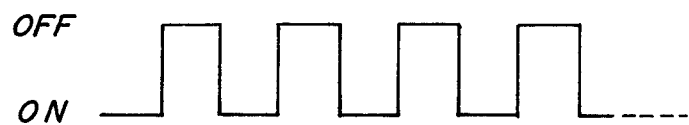
FIGS. 31A, 31B, and 32A, 32B and 32C are waveforms for explaining the operation of the analyzer shown in FIG. 30.
Figure 31B:
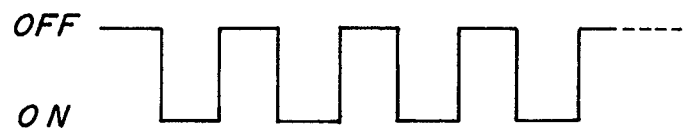
Figure 32A:
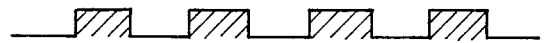
Figure 32B:
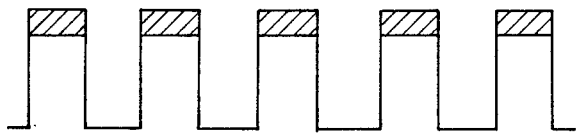
Figure 32C:
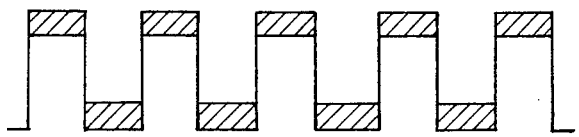

The choppers 66 and 67 are so controlled that the chopped light fluxes have opposite phase as shown in FIGS. 31A and 31B. That is to say, the choppers 66 and 67 are controlled in such a manner that when one of them is made ON, the other is made OFF. Therefore, the monitor signal supplied from a photodiode 8 which detects the chopped light flux 5 via the reference cell 63 and representing various kinds of drifts and the scattered light intensity signal supplied from the photomultiplier 11 and including various kinds of drifts may be shown in FIGS. 32A and 32B, respectively. In these drawings, hatched portions represent components due to the variation in the laser beam emitted from the laser light source 1 and the variation of the standard sample with respect to time. Then the output signals from the photomultiplier 11 and photodiode 8 are summed up by an adder 68 to obtain a sum signal shown in FIG. 31C. The sum signal thus obtained is supplied to a lock-in amplifier 69 controlled by the chopping signal generator 62, there is obtained the signal representing an intensity of the light scattered by the particles 9 in the cell 7 without being influenced by various drifts.

Figure 33:
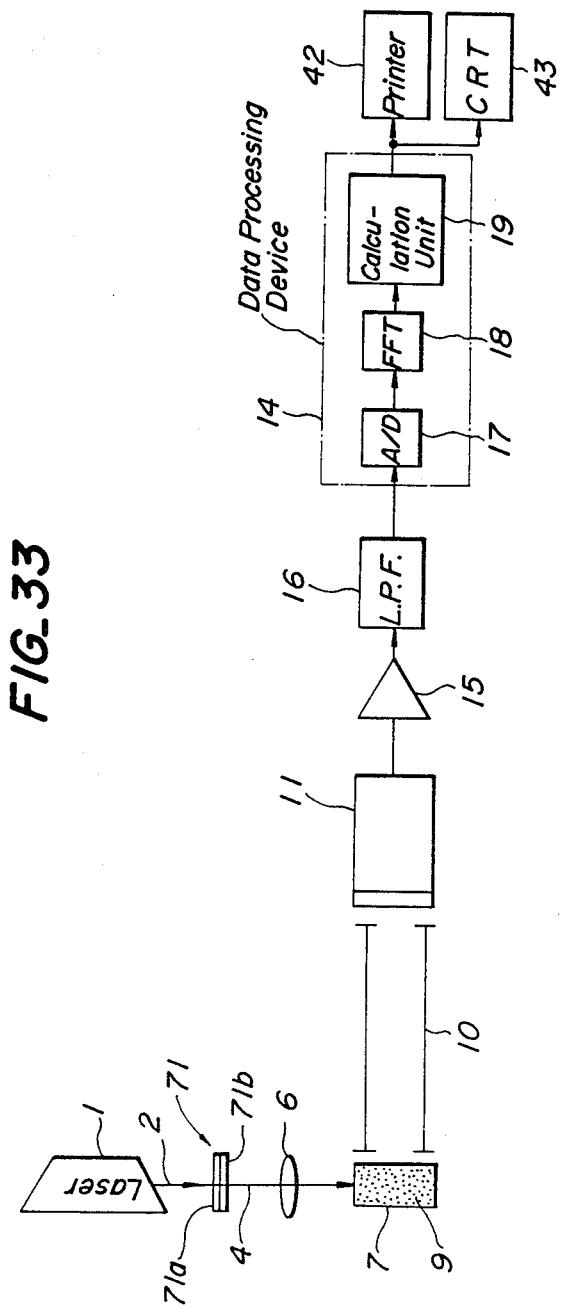
FIG. 33 is a schematic view depicting still another embodiment of the analyzer according to the invention.

FIG. 33 is a schematic view showing still another embodiment of the immunological analyzer according to the invention. In the present embodiment, elements similar to those shown in FIG. 1 are denoted by the same reference numerals as those used in FIG. 1. When use is made of a laser as a light source 1, there might occur the so-called back-talk and the intensity of a light beam 2 emitted from the light source 1 might fluctuate. This is due to the fact that a part of the light beam is reflected by a cell 7 or particles 9 in the cell and is made incident upon the laser light source 1. In the embodiments so far explained, in order to avoid the influence of the fluctuation of the light beam emitted from the laser light source, there is provided the monitoring device. However, such a monitoring device might increase the size and cost of the analyzer. In the present embodiment, between the laser light source 1 and condenser lens 6 is arranged an optical isolator 71 comprising a polarization plate 71a and a quarter wavelength plate 71b. The laser light flux 2 emitted from the laser light source 1 is transmitted through the polarization plate 71a and quarter wavelength plate 71b and then is made incident upon the cell 7 via the condenser lens 6. A light ray reflected by the cell 7 is transmitted through the quarter wavelength plate 71b again and its polarization plane is rotated by 90° with respect to the incident laser light beam. Therefore, the reflected light ray could not be transmitted through the polarization plate 71a. In this manner, according to the present embodiment, it is possible to prevent the reflected light from being incident upon the laser light source 1 and thus the laser beam emitted from the laser light source 1 does not fluctuate due to the back-talk. In this manner, it is possible to derive the signal representing the scattered light intensity at high S/N and therefore, the monitoring device may be completely dispensed with. It should be noted that the optical isolator 71 may be arranged at any desired position between the laser light source 1 and cell 7, and thus the whole analyzer may be made smaller and low cost.

Figure 34:
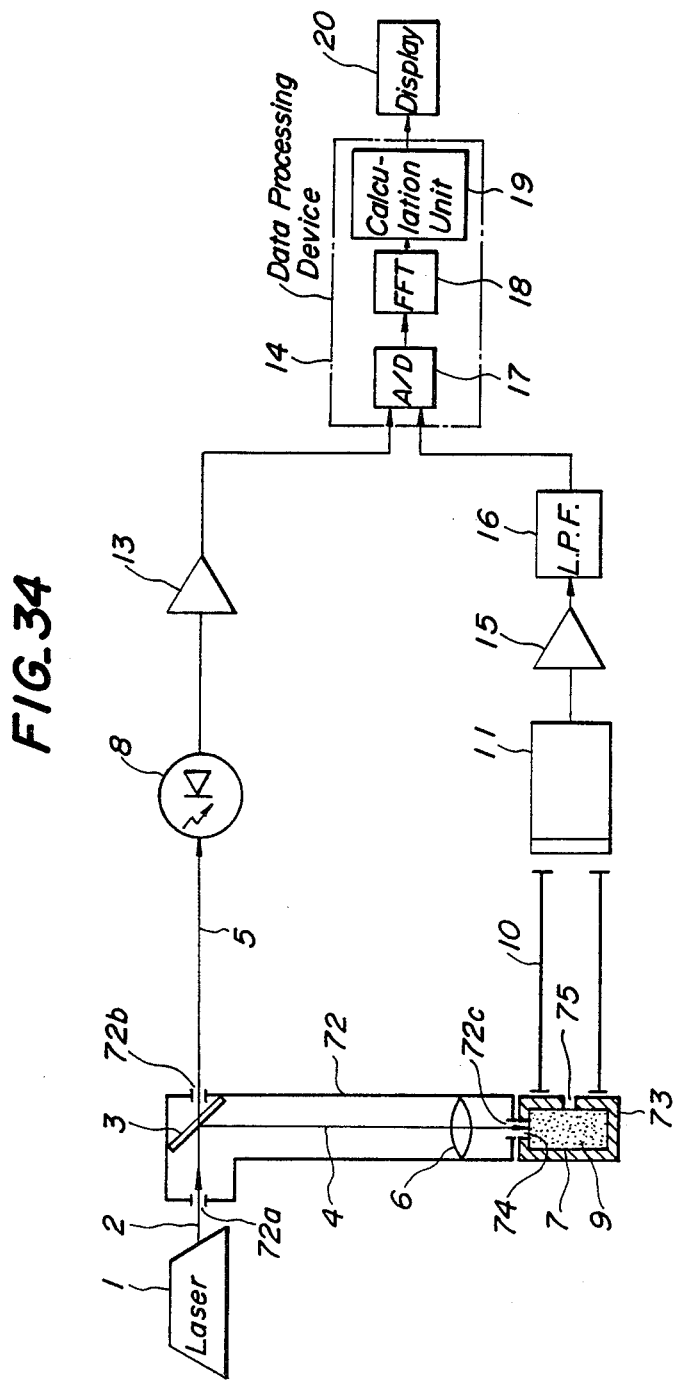
FIG. 34 is a schematic view showing still another embodiment of the analyzer according to the invention.

FIG. 34 is a schematic view showing still another embodiment of the analyzer according to the invention. Also in the present embodiment, portions similar to those illustrated in FIG. 33 are denoted by the same reference numerals used in FIG. 1. In the analyzer according to the invention, it is necessary to detect a relatively weak scattered light flux and thus, if stray light is made incident upon the cell, S/N might be decreased and measuring accuracy might be deteriorated. Particularly, if a light ray reflected by the cell is further reflected by surrounding parts and is made incident again upon the cell, the noise might be increased materially. In order to remove such a drawback, in the present embodiment, an optical path of a light flux 4 from a laser light source 1 to a cell 7 is completely covered with a light guide tube 72. The light guide tube 72 is made of opaque material such as Bakelite and an inner wall is covered with black anti-reflective coating. In end surfaces of the tube 72 are formed openings 72a, 72b and 72c having a small diameter for passing the light fluxes 4 and 5 therethrough. Further, the cell 7 is contained in a cell box 73 made of opaque material. In the cell box 73 are formed entrance hole 74 for introducing the light flux 4 into the cell 7 and an exit hole 75 for projecting the scattered light onto a collimator 10.

FIG. 35 is a perspective view showing the construction of the cell box 73. The cell box 73 is made of black plastic material such as Bakelite and has an inside space in which the cell 7 is intimately inserted. An opening 76 of the inner space may be closed by a slidable lid 77 made of black plastic material. In order to operate the lid 77 manually, the lid is provided with a lever 78 on its upper surface.

FIG. 36 is a perspective view showing another embodiment of the cell box. In the present embodiment, in an elongated box 81 made of opaque material there are formed a plurality of spaces in which a plurality of cells are inserted. Openings of the spaces are closed by means of slidable lids 77-1, 77-2, ... with levers 78-1, 78-2, ... . In a bottom wall of the box 81 are formed a plurality of incident holes 74-1, 74-2, ... and in a side wall of the box 81 there are formed a plurality of exit holes 75-1, 75-2, ... The box 81 may be moved in a direction shown by an arrow A in a stepwise manner manually or automatically. It should be noted that lids 77-1, 77-2, ... may be moved manually or automatically. In this manner, reaction liquids contained in cells 7 set in the inner spaces of the frame like box 81 may be analyzed successively without being affected by stray light.

It should be noted that in the embodiment illustrated in FIG. 34, the light guide tube 72 may be replaced by optical fibers. Moreover, even if the light guide tube 72 is dispensed with, a greater part of the stray light can be avoided only by providing the cell box.

Figure 37:
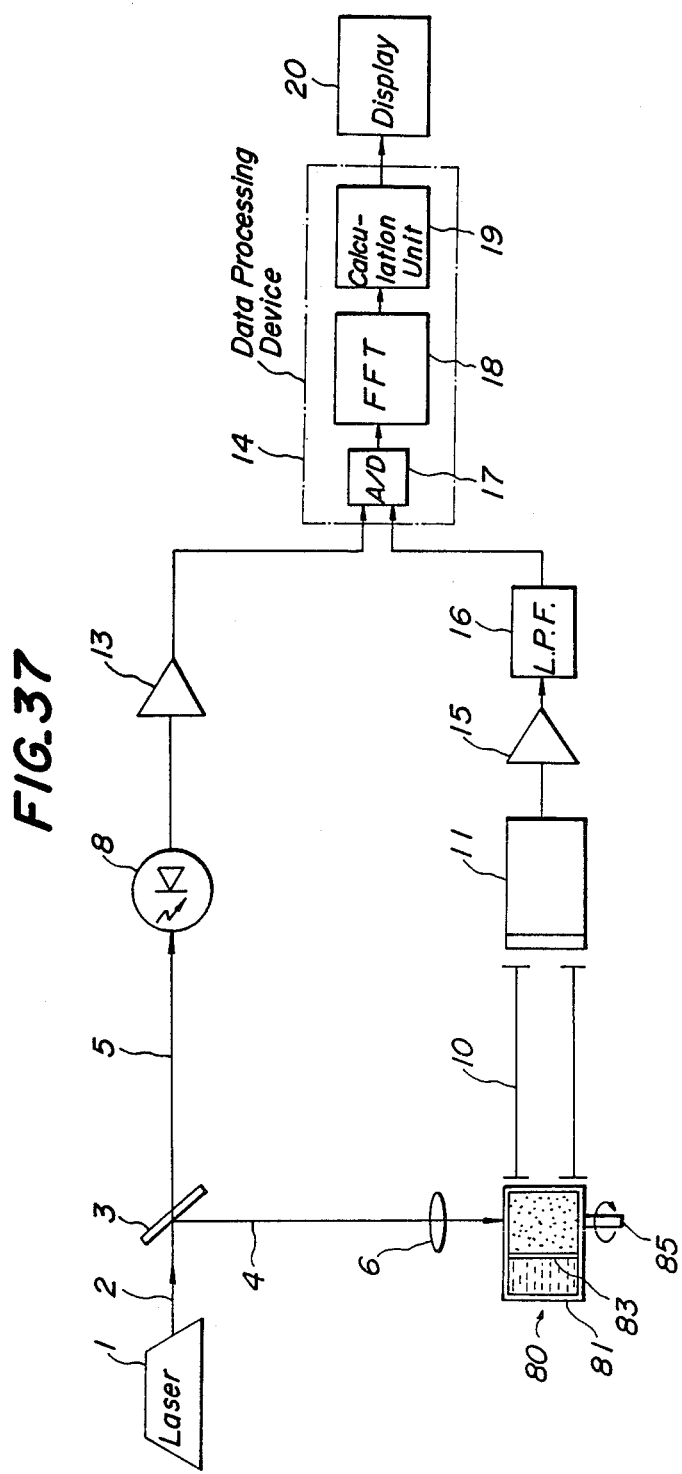
FIG. 37 is a schematic view showing still another embodiment of the analyzer according to the invention.

FIG. 37 is a schematic view showing still another embodiment of the analyzer according to the invention. In the present embodiment, portions similar to those shown in FIG. 1 are denoted by the same reference numerals as those used in FIG. 1 and their explanation is omitted. In this embodiment use is made of a cell 80 having a special construction.

FIG. 38 is a perspective view showing the cell 80. The cell 80 comprises a cell main body 81 made of quartz and having a generally rectangular shape with an upper opening 84 and a lid 82 also made of quartz for closing the opening 84 in a liquid tight manner.

In the main body 81, there is integrally formed a partition 83 whose both side edges are connected to side walls of the main body 81 and whose bottom edge is coupled with a bottom wall of the main body 81. An upper edge of the partition 83 is lower than an upper surface of the main body 81. By means of the partition 83, the inside space of the main body 81 is divided into small chambers 86 and 87. The chamber 86 is called a reaction chamber, whilst the chamber 87 is called a reservoir chamber. On an outer surface of the side wall 81a of the main body 81 is secured a shaft member 85 which extends perpendicularly to the side wall 81a. On an outer surface of the main body 81 except for incident window 88 and exit window 89 is applied black paint. Further on an outer surface of the lid 82 except for an exit window 90 is applied black paint. Through the incident window 88, a laser light beam 4 is made incident upon the cell 80. It should be noted that the shaft member 85 is aligned with an optical axis of the laser light beam 4 transmitted through the incident window 88. The exit windows 89 and 90 serve to transmit the scattered light toward a collimator 10. The cell 80 may be installed in a black box not shown through which the shaft member 85 is extended in such a manner that the cell may be rotated about the shaft member by manually or automatically rotating the shaft member 85 or the cell may be rotated automatically within the black box.

Now the operation of the analyzer of the present embodiment will be explained also with reference to FIGS. 39A to 39C. At first, the cell 80 is set in such a manner that the opening 84 faces upwards as shown in FIG. 39A. Then, a given amount of a reagent, i.e. a buffer solution containing fine particles having antibody or antigen applied thereon, is delivered into the reaction chamber 86 by means of a reagent delivery nozzle 91. Similarly a given amount of a sample containing antigen or antibody to be tested is delivered into the reservoir chamber 87 with the aid of a sample delivery nozzle 92. It should be noted that liquid levels of the reagent and sample have to be lower than the partition 83 so that these liquids are not mixed with each other.

Next, the opening 84 is closed by the lid 82 as illustrated in FIG. 39B, and then the opening of the black box is closed. Then, the intensity of the scattered light before the reaction is measured. In this measurement, the scattered light transmitted through the exit window 89 is made incident upon the photomultiplier 11 by means of the collimator 10.

Then, the cell 80 is rotated by 90° about the shaft member 85 in a direction shown by an arrow A in FIG. 39B. Then the cell 80 is set into a position shown in FIG. 39C. By this rotational movement, the sample in the reservoir chamber 87 is moved into the reaction chamber 86 and is mixed with the reagent to start the reaction.

Immediately after the rotation of the cell 80, the measurement of the variation of the scattered light is commenced. In this measurement, the scattered light transmitted through the exit window 90 provided in the lid 82 is detected as illustrated in FIG. 39C.

The detected intensity of the scattered light is processed by a data processing device 14 comprising A/D converter 17, fast Fourier transformer 18 and calculation unit 19 in the manner explained above with reference to FIG. 1. In this manner, the agglutinated condition of particles contained in the reaction liquid in the reaction chamber 86 can be monitored immediately after the reaction.

As explained above, by using the measuring cell 80 shown in FIG. 38, the mixing of the sample and reagent can be performed by simply rotating the cell without taking the cell out of the analyzer. Therefore, the measurement can be initiated immediately after the reaction.

It should be noted that in case of applying the cell to the heterodyne detection, only a single exit window has to be provided at the position of the shaft member 85. Further, in the cell there may be provided more than two chambers by forming more than one partition.

FIG. 40 is a schematic view shown an embodiment of the automatic immunological analyzer according to the invention. Also in the present embodiment portions similar to those illustrated in FIG. 1 are denoted by the same reference numerals used in FIG. 1. A laser beam 2 emitted from a laser light source 1 is divided into two light fluxes 4 and 5 by means of a beam splitter 3. The light flux 4 is collected by a condenser lens 6 and is made incident upon one of transparent cells 7 which are fed in a stepwise manner along a reaction line in a direction shown by an arrow A. A light flux scattered by particles in a reaction liquid contained in a cell 7 just transported into a measuring position is detected by a photomultiplier 11 via a collimator 10 having a pair of pin holes. The other light flux 5 is made incident upon a silicon photodiode 8 to produce a monitor signal representing a fluctuation of the intensity of the laser beam 2 emitted from the laser light source 1. The output signal from the photomultiplier 11 is supplied to a data processing device 14 via low noise amplifier 15 and low path filter 16. At the same time, the monitor signal from the photodiode 13 is supplied to the data processing device 14 through a low noise amplifier 13. In the data processing device 14, these signals are processed by means of A/D converter 17, fast Fourier transformer 18 and calculation unit 19 to derive a power spectrum density in intensity of light scattered by particles in the reaction liquid. A power spectrum density curve may be displayed on a cathode ray tube 43. Further, measuring results obtained by processing the power spectrum density may be printed out by a printer 42. In this manner a plurality of samples may be analyzed successively by feeding the cells 7 along the reaction line.

Figure 41A:
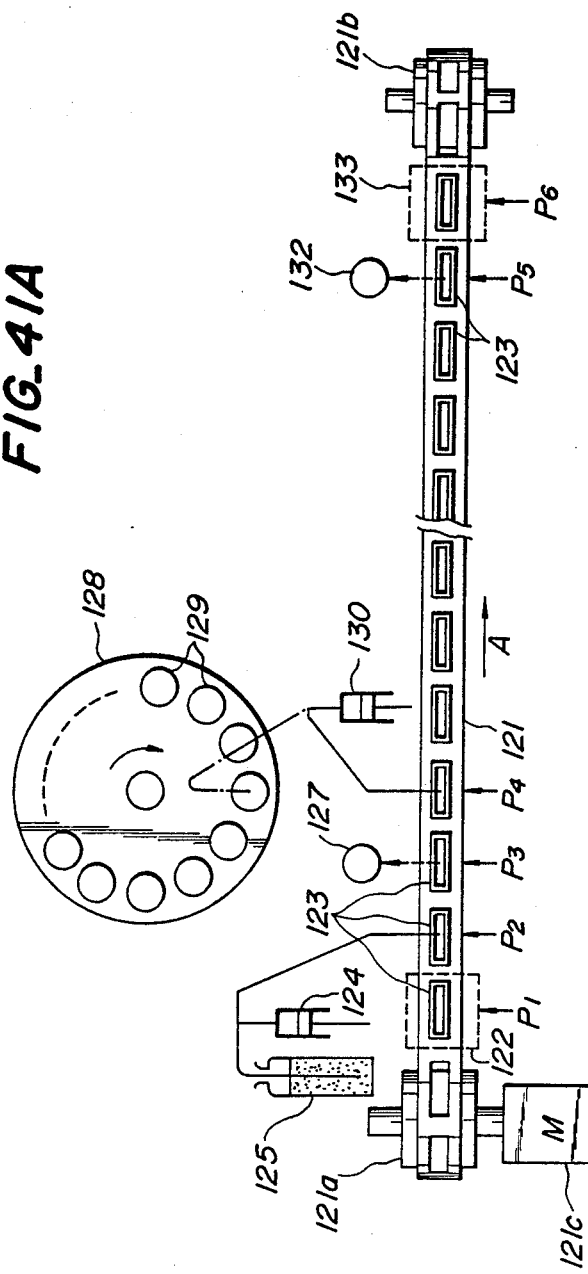
FIGS. 41A and 41B are schematic plan and side views, respectively illustrating an embodiment of the cell transporting mechanism according to the invention.
Figure 41B:
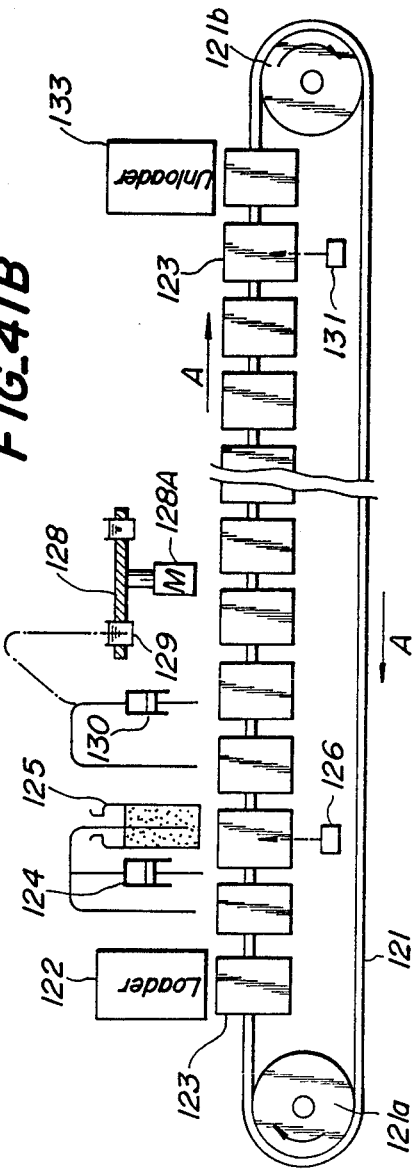

FIGS. 41A and 41B are schematic plan and side views, respectively illustrating an embodiment of the cell transporting mechanism according to the invention. An endless transporting chain 121 is wound between a pair of gears 121a and 121b, and a motor 121c is coupled with the gear 121a. The motor 121c is driven intermittently to move the chain 121 along a reaction line in a direction shown by an arrow A in a stepwise manner. In the chain 121, cells 123 are loaded one by one at a cell loading position $P_1$ by means of a cell loader 122. After that, at a reagent delivery position $P_2$, a given amount of a reagent contained in a reagent vessel 125 is delivered into the cell 123 with the aid of a reagent delivery device 124. The reagent is formed by dispersing in a buffer solution polystyrene latex particles having a diameter of 0.3 $\mu$m, the particles being coated with antibody of immuno globulin G (anti-IgG). At a first photometry position $P_3$, a laser light beam emitted from a laser light source 126 is made incident upon a bottom surface of the cell 123 and a scattered light emanating from a side wall of the cell 123 is detected by a photodetector 127 to derive a power spectrum density prior to the reaction. Next, at a sample delivery position $P_4$, a given amount of a sample is delivered into the cell 123. Samples are contained in sample cups 129 which are arranged along a periphery of a turntable 128 which is rotated by a motor 128a in synchronism with the chain 121. Successive samples in the sample cups 129 are delivered into successive cells 123 in the chains 121 by means of a sample delivery device 130. When the sample is delivered into the cell, the antigen-antibody reaction is initiated.

After a given time period, at a second photometry position $P_5$, a laser light beam emitted from a laser light source 131 is made incident upon the cell 123 via its bottom wall and a scattered light flux is detected by a photodetector 132 to derive a power spectrum density after the reaction. After the measurement, the cell 123 is removed from the chain 121 by means of a cell unloader 133 at a cell removing position $P_6$.

As explained above, in the analyzer of the present embodiment, successive samples are delivered into successive cells and the immunological reaction in successive reaction liquids is measured. In this manner, successive samples can be measured automatically in an efficient manner. As explained above, the transporting chain 121 is moved intermittently and its stationary time is determined mainly by a time required for collecting photometry data and processing the collected data. Further a distance between the sample delivery position $P_4$ and second photometry position $P_5$ is determined in accordance with a necessary reaction time. For instance, when the data collecting and processing time is five minutes, and the necessary reaction time is sixty minutes, there are provided twelve pitches between the positions $P_4$ and $P_5$.

FIGS. 42A and 42B are schematic plan and cross-sectional views, respectively showing another embodiment of the automatic analyzer according to the invention. In the present embodiment, a number of flat cells 141 are arranged along a periphery of a turntable 142 which is rotated intermittently in a direction shown by an arrow A. The turntable 142 is arranged above a thermostat 143 in which a clear thermostat liquid 144 is contained, and liquids in the cells 141 are kept at a desired reaction temperature. On a bottom wall of the thermostat 143 is secured an ultrasonic vibrating element 145. Then particles, in reaction liquids contained in the cells 141 are excited by ultrasonic energy and are agitated effectively. Therefore, the probability that antigen and antibody are reacted with each other is increased, and thus the reaction time may be shortened. This is particularly effective for a sample having a low antigen or antibody concentration.

While the turntable 142 is rotated intermittently, at a position $P_1$ a given amount of a reagent contained in a reagent vessel 147 is delivered into a cell 141 by means of a reagent delivery device 146. Next, at a position $P_2$, a first photometry is effected to derive a power spectrum density before the reaction. To this end, a laser light beam emitted from a laser light source 148 is guided by means of an optical fiber 149 into a position inside the thermostat 143, and is made incident upon a bottom wall of the cell 141. A scattered light flux emanating from a side wall of the cell 141 is guided by means of an optical fiber 150 into a photodetector 151 arranged outside the thermostat 143.

After deriving the power spectrum density prior to the reaction, a given amount of a sample is delivered into the cell 141 by means of a sample delivery device 152. Samples are contained in sample vessels 153 and are transported on a transporting member 154 in a direction depicted by an arrow B in synchronism with the turntable 143. In the present embodiment, in order to enhance the processing faculty, the second photometry is performed at the position $P_2$ after the turntable 143 is rotated by one revolution. Therefore, the number of cells 141 arranged on the turntable 143 and the rotation speed of the turntable have to be determined in accordance with a necessary reaction time. In general, when a sample has a low antigen or antibody concentration, the reaction time becomes longer and the turntable 143 is rotated by one revolution during this long reaction time. However, in the present embodiment, since particles are effectively agitated by the ultrasonic vibrating element 145, the reaction time can be made shorter, and therefore the processing speed can be increased. Moreover, in the present embodiment, since it is sufficient to provide only one set of the laser light source 148 and photodetector 151, the whole construction of the analyzer can be made simple.

It should be further noted that the time required for one revolution of the turntable 143 may be set to the shortest reaction time, instead of the longest reaction time. In such a case, after one revolution of the turntable 143, the first power spectrum density is measured and the data is checked whether or not useful data has been obtained. If no useful data is obtained, the second power spectrum density is measured after the turntable has rotated further by one revolution, and then the data is checked again. The above process is repeated until useful data is obtained. In such an analyzer, cell autoloader and unloader or a cell washing device has to be operated independently for respective cells.

FIGS. 43A and 43B illustrate still another embodiment of the automatic analyzer according to the invention. In the present embodiment, portions similar to those shown in FIGS. 42A and 42B are denoted by the same reference numerals used in FIGS. 42A and 42B. In this embodiment, at a position $P_1$, a given amount of a reagent is delivered into a cell 141 by means of a reagent delivery device 147, and a measurement prior to the reaction is performed. Next at a position $P_2$ a given amount of a sample contained in a sample vessel 153 is delivered into the cell 141 by means of a sample delivery device 152 to initiate the antigen-antibody reaction. After the turntable 142 has rotated almost one revolution, when the relevant cell 141 is transported into a position $P_3$, a measurement is carried out. In the present embodiment, a time necessary for the turntable rotating from $P_2$ to $P_3$ is set to the longest reaction time. After the measurement has been completed at the position $P_3$, the relevant cell is removed from the turntable 142 and a new cell is set in the turntable. In this manner, successive samples can be measured effectively.

In this embodiment, the photometry is effected at the positions $P_1$ and $P_2$, but there is provided only one set of laser light source 148 and photodetector 151. That is to say, the laser light source 148 is arranged underneath the cells 141 and a laser light beam emitted from the laser light source 148 is made incident upon a half mirror 160 arranged rotatably. A light flux transmitted through the half mirror 160 is detected by a photodiode 161 to generate a monitor signal representing a fluctuation of the laser light beam emitted from the laser light source 148. When the photometry is to be effected at the position $P_1$, a light flux reflected by the half mirror 160 is further reflected by a reflection mirror 162 and 163 and is then made incident upon a cell 141 situating at the position $P_1$ via an air bath type thermostat 143. Therefore, an ultrasonic vibrating element 145 is provided on the turntable 142. A light flux scattered by particles in the cell is made incident upon the photodetector 151 by means of a sector shape collimator 164 having two incident pin holes 164a and 164b and exit pin hole 164c. In case of performing the photometry at the position $P_3$, the half mirror 160 is rotated into a position shown by a chain line and a light flux reflected by the half mirror is made incident upon a cell 141 situating at the second position by means of a reflection mirror 163. Then a light flux scattered by particles is made incident upon the photodetector 151 via the pin holes 164b and 164c of the collimator 164. In this manner, according to the invention, the photometry can be performed selectively at the positions $P_1$ and $P_3$.

The present invention is not limited to the embodiments mentioned above, but may be modified in various manner. In the above embodiment, immuno globulin G (IgG) is used as the antigen to be tested, but any other substances such as immuno globulin A (IgA), IgM, IgD, IgE, Australia antigen, and insurine which cause agglutination by the antigen-antibody reaction. Further, in the above embodiments, antibody is bound on the particle surface and antigen in a test sample is measured, but antibody in a test sample may be detected by using particles having antigen bounded thereon. In the above embodiments, use is made of polystyrene latex particles, but any other organic particles and inorganic particles such as glass beads may be used. Moreover, in the above embodiments, particles are existent in the test solution before the reaction, but it is also possible to utilize particulate substances which are produced by the antigen-antibody reaction. For instance, when human villus gonadotropin (HCG) is used as antigen and anti-human villus gonadotropin (anti-HCG) is used as antibody, then antigen-antibody complex produced by the antigen-antibody reaction can be used as particles. Further, antigen itself may be used as particle. An example of such antigen-antibody reaction is a reaction in which candida albicans (yeast) is used as antigen and anti-candida albicans is used as antibody. Moreover, blood corpuscles, cells and microorganisms may be used as particles. Further in the embodiment shown in FIG. 1, the measurement is carried out by the batch system in which test solutions are successively poured into the cell, but use may be made of a flow system in which antigen-antibody reaction liquid is continuously flowed through the cell. It should be further noted that in the embodiments so far explained the light source is formed by the laser light source emitting coherent light, but any light source emitting incoherent light may be also used.

The advantageous effects obtained by the present invention may be summarized as follows.

(1) Since reagents such as enzyme and radio isotope which is expensive and difficult for handling are not used, the analysis can be performed economically and easily.

(2) Since the precision and reproducibility of the method according to the invention are higher than those of the non-labeling immunological analyses such as immuno electrophoresis, immuno diffusion and sedimentation, it is possible to obtain reliable measurement results at high precision.

(3) Since the measurement is performed by detecting the fluctuation in intensity of scattered light due to the Brownian motion of particles, it is possible to effect the precise measurement within a short time period even if an amount of a sample to be tested is extremely small.

(4) Upon comparing the known method in which the mean diffusion constant is detected from the variation of the spectral width of the scattered light, according to the invention the spectrometer is not required at all. Therefore, the whole measuring apparatus can be made small in size and cheap in cost, and further it is possible to obtain highly precise and reliable measuring results.

(5) Since the measurement is based on the power spectrum density of fluctuation in intensity of scattered light, it is possible to derive a large amount of useful information about the antigen-antibody reaction.

(6) In the embodiments of the analyzer in which particles in reaction liquids are agitated by the ultrasonic energy, the reaction can be promoted effectively and therefore the reaction time can be shortened even if the concentration of antigen or antibody to be tested is small. Moreover, the accuracy of measurement can be increased.

(7) In the embodiments of the analyzer in which a mean power spectrum density is derived by averaging a plurality of power spectrum densities obtained with the aid of a plurality of channels, S/N can be made high extremely and the accuracy and reliability of measurement can be increased to a great extent.

(8) Further, in the embodiments of the analyzer in which the incident light beam is chopped and the output signal from the photodetector is processed by the lock-in amplifier, the accurate measurement can be performed without being affected by drift and background noise.

(9) In the embodiment of the analyzer in which the optical isolator and quarter wavelength plate are provided in the incident optical path, the fluctuation of light emitted from the laser light source due to the back talk can be effectively avoided.

(10) In the embodiments of the analyzer in which the cell and incident optical path are covered with the opaque boxes, the measurement can be effected accurately without being affected by stray light.

(11) In the embodiment of the analyzer in which the reaction is initiated by rotating the measuring cell having a plurality of chambers divided by the partition, the photometry can be effected easily from the start of reaction.

(12) In the embodiments of the automatic analyzer, successive samples can be measured automatically in an accurate and efficient manner.

What is claimed is:

1. A method of measuring immunological reaction comprising the steps of:
    projecting radiation to a reaction liquid containing at least antigen and antibody;
    detecting radiation scattered by particulate substances in the reaction liquid;
    deriving a plurality of power spectrum densities of fluctuation in intensity of said scattered radiation;
    deriving a mean power spectrum density in accordance with said plurality of power spectrum densities; and
    measuring antigen-antibody reaction on the basis of said mean power spectrum density.

2. A method according to claim 1, wherein said plurality of power spectrum densities are derived by sampling the scattered radiation by plural times at different time instances.

3. A method according to claim 1, wherein said plurality of power spectrum densities are derived by detecting simultaneously the radiation scattered from different points in the reaction liquid with the aid of a plurality of radiation detectors.

4. A method according to claim 3, wherein said radiation is projected into the reaction liquid in such a manner that the radiation is focused in the reaction liquid to form a focus line, and the radiation scattered by different points on the focus line is simultaneously detected by said plurality of radiation detectors.

5. A method according to claim 3, wherein said radiation is projected into the reaction liquid in such a manner that a parallel radiation is transmitted through the reaction liquid, and radiation scattered at different points on the parallel radiation.

6. An apparatus for measuring an immunological reaction comprising:
    a light source for emitting a light flux;
    a cell for containing an antigen-antibody reaction liquid;
    optical means for projecting the light flux emitted from the light source into said cell;
    detecting means for receiving light scattered by particulate substance included in said antigen-antibody reaction liquid and for deriving a plurality of power spectrum densities of fluctuation in intensity of said scattered light;
    means for deriving a mean power spectrum density from said plurality of power spectrum denisities; and
    means for measuring an immunological reaction in the antigen-antibody reaction liquid on the basis of the mean power spectrum density.

7. An apparatus according to claim 6, wherein said detecting means for deriving a plurality of power spectrum densities comprising
    a photodetector for generating a photoelectric signal representing the scattered light;
    an A/D converter for sampling the photoelectric signal at different time instances to produce a plurality of digital signals;
    a fast Fourier transformer calculating the digital signals to derive a plurality of power spectrum densities successively;
    memory means for storing said plurality of power spectrum densities; and means for averaging a plurality of power spectrum densities to produce the mean power spectrum density.

8. An apparatus according to claim 6, wherein said detecting means comprises
- a plurality of photodetectors for receiving simultaneously light rays scattered at different positions in the cell to produce a plurality of photoelectric signals;
- a plurality of A/D converters for converting said plurality of photoelectric signals into a plurality of digital signals;
- first storing means for storing said plurality of digital signals;
- a fast Fourier transformer for successively receiving said plurality of digital signals to derive successively a plurality of power spectrum densities;
- a second storing means for storing said plurality of power spectrum densities; and
- means for averaging said plurality of power spectrum densities read out of said second storing means to derive a mean power spectrum density.

9. An apparatus according to claim 8, wherein said detecting means further comprises a plurality of collimators arranged between the cell and the photodetectors.

10. An apparatus according to claim 9, wherein said plurality of collimating means comprises an optical fiber array.

11. An apparatus according to claim 10, wherein an incident end portion of said optical fiber array is penetrated into the cell.

12. An apparatus according to claim 9, wherein said collimating means comprises an imaging lens for forming an image of said different points in the cell onto the photodetectors.

13. An apparatus according to claim 12, wherein said imaging lens is composed of a cylindrical lens.

14. An apparatus according to claim 8, wherein said optical means comprises a cylindrical lens for focusing the light flux emitted from the light source within the cell to form a focus line.

15. An apparatus according to claim 8, wherein said optical means comprises a collimator lens for projecting the light beam emitted from the light source into the cell as a parallel light beam.

16. An apparatus according to claim 7, further comprising means for detecting a part of the light beam emitted from the light source to generate a monitor signal representing a fluctuation of the light beam, and means for normalizing the photoelectric signal in accordance with the monitor signal.

17. An apparatus according to claim 9, wherein said collimating means comprises an optical fiber array having an incident side arranged in opposite to the cell and an exit side, and a linear channel-plate type image intensifier having an incident side arranged in opposite to the exit side of the image intensifier and an exit side arranged in opposite to the photodetectors.

18. An apparatus according to claim 9, wherein said collimating means comprises a plurality of discrete optical fibers arranged between the cell and the photodetectors.

19. An apparatus according to claim 9, wherein said collimating means comprises an optical fiber array having an incident side and an exit side arranged in opposite to the photodetectors, and an imaging lens for forming an image of the different points in the cell onto the incident side of the optical fiber array.

20. An apparatus for measuring an immunologial reaction comprising:
- a light source for emitting a light flux;
- a cell for containing an antigen-antibody reaction liquid;
- optical means for projecting the light flux emitted from the light source into said cell;
- detecting means for receiving light scattered by particles included in said reaction liquid to produce a photoelectric signal;
- means for receiving the photolectric signal and measuring an immunological reaction in the antigen-antibody reaction liquid in accordance with a power spectrum density of fluctuation in intensity of the scattered light; and
- means for applying ultrasonic energy to the reaction liquid during said immunological reaction to vibrate the particles in the reaction liquid thereby promoting said immunological reaction.

21. An apparatus according to claim 20, wherein said ultrasonic wave applying means comprises an ultrasonic vibrating element secured to an outer surface of the cell.

22. An apparatus according to claim 20, further comprising a thermostat including a vessel and a thermostat liquid contained in the vessel, said cell being immersed in said thermostat liquid, and wherein said ultrasonic energy applying means comprises an ultrasonic vibrating element secured to an outer surface of the vessel.

23. An apparatus according to claim 20, wherein said ultrasonic wave applying means comprises an ultrasonic vibrating element arranged movably between a first position in which the ultrasonic vibrating element is spaced from the cell and a second position in which the ultrasonic vibrating element is brought into contact with the cell.

24. An apparatus according to claim 21, wherein said cell is moved along a reaction line, and said ultrasonic wave applying means further comprises conductive brushes connected to the ultrasonic vibrating element and conductive rails arranged along the reaction line, said conductive brushes being brought into contact with the conductive rails.

25. An apparatus according to claim 20, wherein said ultrasonic wave applying means generates the ultrasonic wave having a frequency which is sufficiently remote from frequency components of the fluctuation of scattered light.

* * * * *

UNITED STATES PATENT AND TRADEMARK OFFICE
CERTIFICATE OF CORRECTION

PATENT NO. : 4,762,413

DATED : August 9, 1988

INVENTOR(S) : Akihiro NAMBA; Fumio UCHINO; Hitoshi TATEOKA; Masahiro OHNO; Kouichi KARAKI; Tatsuo NAGASAKI It is certified that error appears in the above-identified patent and that said Letters Patent is hereby corrected as shown below:

Front page, under Section [30] Foreign Application Priority Data, line 6, change "59-186253" to --59-187253--.

Signed and Sealed this

Twenty-third Day of May, 1989

Attest:

DONALD J. QUIGG

Attesting Officer

Commissioner of Patents and Trademarks